US012589093B2

(12) United States Patent
Babu et al.

(10) Patent No.: US 12,589,093 B2
(45) Date of Patent: Mar. 31, 2026

(54) PLASMA KALLIKREIN INHIBITORS AND METHODS OF USE THEREOF IN OCULAR DISORDERS

(71) Applicant: BIOCRYST PHARMACEUTICALS, INC., Durham, NC (US)

(72) Inventors: Yarlagadda Babu, Birmingham, AL (US); Viral Kansara, Alpharetta, GA (US); Rick McElheny, Alpharetta, GA (US)

(73) Assignee: BIOCRYST PHARMACEUTICALS, INC., Durham, NC (US)

( * ) Notice: Subject to any disclaimer, the term of this patent is extended or adjusted under 35 U.S.C. 154(b) by 1029 days.

(21) Appl. No.: 17/602,674

(22) PCT Filed: Apr. 8, 2020

(86) PCT No.: PCT/US2020/027287

§ 371 (c)(1),
(2) Date: Oct. 8, 2021

(87) PCT Pub. No.: WO2020/210368

PCT Pub. Date: Oct. 15, 2020

(65) Prior Publication Data

US 2022/0160694 A1 May 26, 2022

Related U.S. Application Data

(60) Provisional application No. 62/830,802, filed on Apr. 8, 2019.

(51) Int. Cl.

| | |
|---|---|
| ***A61K 31/4418*** | (2006.01) |
| ***A61K 9/00*** | (2006.01) |
| ***A61P 27/02*** | (2006.01) |
| ***C07K 16/40*** | (2006.01) |

(52) U.S. Cl.

CPC ........ *A61K 31/4418* (2013.01); *A61K 9/0019* (2013.01); *A61K 9/0048* (2013.01); *A61P 27/02* (2018.01); *C07K 16/40* (2013.01)

(58) Field of Classification Search

CPC .............. A61K 31/4418; A61K 9/0019; A61K 9/0048; A61P 27/02

See application file for complete search history.

(56) References Cited

U.S. PATENT DOCUMENTS

| | | | | |
|---|---|---|---|---|
| 2015/0274841 | A1 | 10/2015 | Conley et al. | |
| 2015/0368359 | A1 | 12/2015 | Belichard | |
| 2016/0310417 | A1* | 10/2016 | Prausnitz | A61K 39/3955 |
| 2017/0266172 | A1 | 9/2017 | Babu et al. | |
| 2018/0028516 | A1 | 2/2018 | Zarnitsyn et al. | |
| 2018/0296525 | A1* | 10/2018 | Roizman | A61K 31/40 |
| 2018/0354906 | A1 | 12/2018 | Kotian et al. | |
| 2019/0015521 | A1 | 1/2019 | Roizman | |

FOREIGN PATENT DOCUMENTS

| | | |
|---|---|---|
| JP | 2017-525718 A | 9/2017 |
| WO | 2016/029214 | 2/2016 |
| WO | 2018/081513 A1 | 5/2018 |

OTHER PUBLICATIONS

"Eye Diseases: What Should I Know about Them?" Cleveland Clinic, Mar. 19, 2025. https://my.clevelandclinic.org/health/diseases/eye-diseases. (Year: 2025).*

Extended European Search Report received for European Patent Application No. 20786941.3, mailed on Dec. 15, 2022, 08 pages.

International Preliminary Report on Patentability received for International Patent Application No. PCT/US2020/027287, mailed on Oct. 21, 2021, 9 pages.

International Search Report and Written Opinion received for International Patent Application No. PCT/US2020/027287, mailed on Jul. 1, 2020, 13 pages.

Notice of Refusal for Japanese Patent Application No. 2021-559442, mailed Mar. 26, 2024, 6 Pages including English Translation.

Zhang et al., "Discovery of Highly Potent Small Molecule Kallikrein Inhibitors", Med chem., vol. 2, Issue 6, 2006, pp. 545-553.

Office Action received for Canadian Patent Application No. 3136326, mailed on Feb. 16, 2024, 4 Pages.

* cited by examiner

*Primary Examiner* — James H Alstrum-Acevedo
*Assistant Examiner* — Carolyn L. Ladd
(74) *Attorney, Agent, or Firm* — Nicholas J. Landau; Erin Gaddes; Maynard Nexsen PC

(57) ABSTRACT

This disclosure is generally in the field of ophthalmic therapies, and more particularly to the treatment of various ocular diseases and conditions by non-surgical administration to the eye of a subject of a drug composition described herein containing a plasma kallikrein inhibitor. Plasma kallikrein inhibitors include avoralstat. The compositions and methods include delivery of a plasma kallikrein inhibitor to the suprachoroidal space (SCS) of the eye.

16 Claims, 6 Drawing Sheets

Day 28: N=1 (3 samples BLQ)
Day 14: N=2 (2 samples BLQ)

day 10, n=3 samples BLQ
day 3, 7, 14, 21, 28, 56, 84 all samples BLQ

PLASMA KALLIKREIN INHIBITORS AND METHODS OF USE THEREOF IN OCULAR DISORDERS

CROSS-REFERENCE TO RELATED APPLICATIONS

This application is a national stage under 35 U.S.C. 371 of International Application No. PCT/US2020/027287, filed on Apr. 8, 2020 (currently published). International Application No. PCT/US2020/027287 cites the priority of U.S. Patent Application No. 62/830,802, filed Apr. 8, 2019.

BACKGROUND OF THE DISCLOSURE

The anterior region of the eye refers to the front portion of the eye (i.e., the portion of the eye in front of, and including, the lens), and includes structures in front of the vitreous humor such as the cornea, iris, ciliary body and lens. The posterior segment of the eye refers to the back portion of the eye (i.e., the portion of the eye behind the lens), and includes the vitreous humor, the sclera, the choroid, the Bruch's membrane, the retinal pigment epithelium, the subretinal space, the retina, the macula, the optic disk, the optic nerve, the ciliary body, and/or the trabecular meshwork. The sclera (a.k.a., the white of the eye) is an opaque, fibrous, protective outer layer of the eye. The sclera includes connective tissue that maintains the shape of the eye by offering resistance to internal and external forces. The suprachoroidal space is the area between the sclera and choroid in the posterior segment of the eye.

The delivery of drugs to the eye is extremely difficult, particularly to the posterior segment of the eye. Many inflammatory and proliferative diseases in the posterior segment of the eye require long term pharmacological treatment. Examples of such diseases include macular degeneration, diabetic macular degeneration, diabetic retinopathy, and others. The current long term pharmacological treatments of such disorders can result in various adverse effects and adverse clinical manifestations, both locally in the eye and systemically.

Although there are known methods of delivery of drugs into the posterior segment of the eye, it is often difficult to deliver effective doses of a drug to the posterior segment of the eye using conventional delivery methods and drug formulations. Delivery methods for drug formulations to the eye include topical application, intravitreal administration (IVT), intracameral administration, systemic administration, and administration to the suprachoroidal space. While each of these methods offers clinical utility for the treatment of certain diseases and conditions, not all of these methods are suitable for delivery of a drug to the posterior segment of the eye. Topical applications, such as eye drops, are useful in treating conditions affecting the exterior surface of the eye or tissues at the front of the eye, however, eye drops are often not sufficiently conveyed to the posterior segment of the eye. Due to the limited half-life of many compounds in the vitreous, IVT administration generally requires multiple injections which increases the risk of cataract, retinal detachment, elevated intraocular pressure, hemorrhage and endophthalmitis. The delivery of drug formulations to the posterior segment of the eye through systemic administration is limited by the outer and inner blood-retinal barriers and reduced therapeutic potency due to the dilution and degradation of the drug before reaching the posterior segment of the eye. Delivery to the suprachoroidal presents an attractive delivery methods for drugs to the posterior segment of the eye. However, even for this mode of administration the half-life of many drugs is such that repeated injections are required (for example every 1 to 2 months) and the concentration of the drug is below the levels needed for effective treatment.

It would be desirable to provide better, safer, more effective therapies for the treatment of various eye diseases and conditions, including diseases and conditions of the posterior segment of the eye. The present disclosure addresses these and other needs.

SUMMARY OF THE DISCLOSURE

The present disclosure provides a method for treating an ocular disease or condition in a subject, the method comprising non-surgically administering a drug composition comprising an effective amount of a compound of the disclosure to the suprachoroidal space (SCS) of the eye of the subject. In some embodiments, the methods described incorporate the novel drug compositions comprising a compound of the disclosure as described herein.

The compounds of the disclosure are plasma kallikrein inhibitors. In some embodiments, the compound of the disclosure is a small molecule plasma kallikrein inhibitor. In some embodiments, the compound of the disclosure is BCX4161. In some embodiments the compound of the disclosure is an inhibitory peptide or an anti-plasma kallikrein antibody. In some embodiments, the drug composition is administered to the SCS of the eye via a puncture member, such a, but not limited to, a microneedle.

In some embodiments, the method for treating an ocular disease or condition in a subject comprises non-surgically administering a drug composition comprising an effective amount of a compound of the disclosure to the SCS of the eye of the subject provides a therapeutic benefit in the treatment of the ocular disease or condition in the absence of a local and/or a systemic side effect.

In some embodiments, the method for treating an ocular disease or condition in a subject in need thereof comprising non-surgically administering a drug composition comprising an effective amount of a compound of the disclosure to the SCS of the eye of the subject provides a favorable ocular PK profile (for example, an increased concentration of the compound of the disclosure in the SCS or an ocular tissue).

In some embodiments, the compound of the disclosure reaches the sclera, the choroid, the Bruch's membrane, the retinal pigment epithelium, the subretinal space, the retina, the macula, the optic disk, the optic nerve, the ciliary body, and/or the trabecular meshwork after administration to the SCS using the methods disclosed herein. In some embodiments, the compound of the disclosure reaches the choroid, retinal pigment epithelium, sclera, retina, the optic nerve, the peripheral retinal pigment epithelium, the peripheral choroid, the peripheral sclera, the peripheral retina, the central retinal pigment epithelium, the central choroid, the central sclera, and/or the central retina, after administration using the methods disclosed herein.

In some embodiments, high levels of the compound of the disclosure reach the sclera, the choroid, the Bruch's membrane, the retinal pigment epithelium, the subretinal space, the retina, the macula, the optic disk, the optic nerve, the ciliary body, and/or the trabecular meshwork after administration to the SCS using the methods disclosed herein. In some embodiments, high levels of the compound of the disclosure reach the choroid, RPE, sclera, retina, and/or optic nerve after administration to the SCS using the methods disclosed herein.

In some embodiments, the compound of the disclosure is retained in the choroid, RPE, sclera, and/or retina for an extended length of time. For example, in some embodiments, the plasm kallikrein inhibitor is retained in the choroid, RPE, sclera, and/or retina for at least about 7, 14, 21, 28, 35, 42, 49, 56, 63, 70, 90, or more days after administration. In some embodiments, the plasm kallikrein inhibitor is retained in the the choroid, retinal pigment epithelium, sclera, retina, the optic nerve, the peripheral retinal pigment epithelium, the peripheral choroid, the peripheral sclera, the peripheral retina, the central retinal pigment epithelium, the central choroid, the central sclera, and/or the central retina for at least about 7, 14, 21, 28, 35, 42, 49, 56, 63, 70, 90, or more days after administration.

In some embodiments, the compound of the disclosure is targeted to the posterior segment of the eye. For example, in some embodiments, the compound of the disclosure is not retained in in a significant amount in the vitreous humor. For example, in some embodiments, the drug levels in the vitreous humor drop by about 1, 2, 3, 4, 5, 6, 7, 8, 9, 10, 11, 12, 13, or 14 days after administration. Thus, in some embodiments, the methods provided herein achieve high levels of the compound of the disclosure in the posterior segment of the eye with limited exposure in the anterior segment of the eye.

In some embodiments, the methods provided herein result in minimal or no systemic exposure to the compound of the disclosure.

In some embodiments, the method for treating an ocular disease or condition in a subject in need thereof comprises non-surgically administering an effective amount of a compound of the disclosure to the SCS of the eye of the subject and administering an additional therapeutic agent to the eye of the subject.

In some embodiments, the ocular disease or condition is selected from the group consisting of retinopathy, macular degeneration, uveitis, macular edema, diabetic macular edema (DME), scleritis, retinitis, and choroiditis. In some embodiments, the macular degeneration is selected from the group consisting of age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, subfoveal wet age-related macular degeneration, and vitreomacular adhesion associated with neovascular age related macular degeneration.

In some embodiments, the ocular disease or condition is retinopathy, wherein the retinopathy is selected from the group consisting of diabetic retinopathy, hypersensitive retinopathy, sickle cell retinopathy, retinopathy of prematurity, and central serous retinopathy.

In some embodiments, the ocular disease or condition is a neovascular condition of the eye. In further embodiments, the neovascular condition of the eye is selected from the group consisting of aberrant ocular angiogenesis, ocular neovascularization, choroidal neovascularization, and polypoidal choroidal vasculopathy.

In some embodiments, the ocular disease or condition affects the posterior segment of the eye. In some embodiments, the ocular disease or condition is a diabetic eye disease. In some embodiments, the ocular diseases or condition is macular degeneration. In some embodiments, the ocular disease is diabetic macular degeneration. In some embodiments, the ocular disease is diabetic macular edema. In some embodiments the ocular disease is diabetic retinopathy.

DETAILED DESCRIPTION

Figure 1:
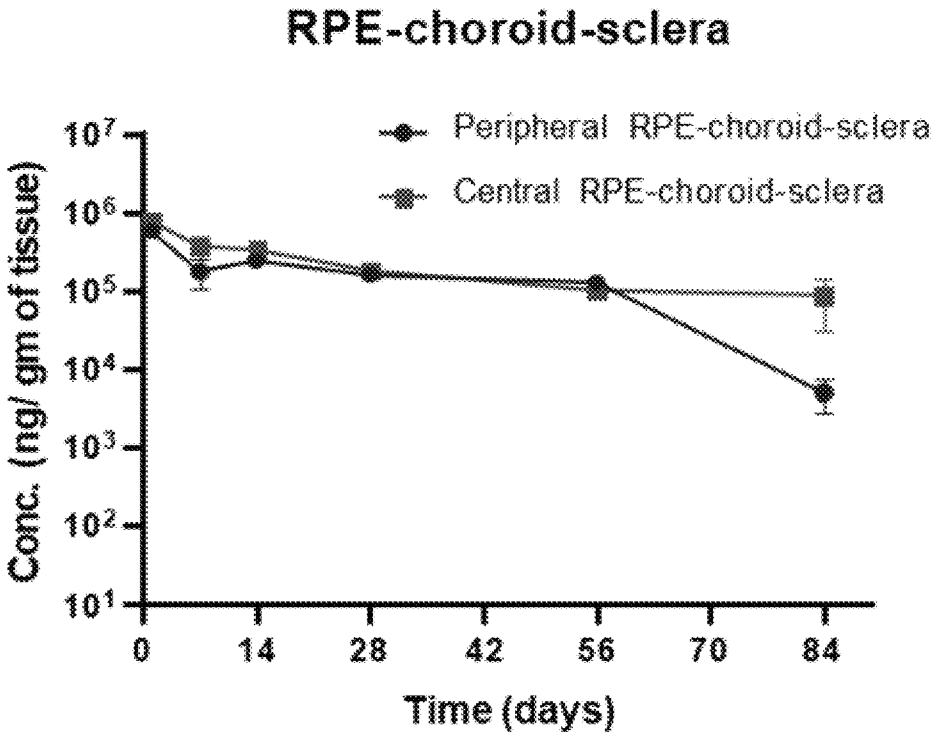
FIG. 1 shows drug concentration (ng/gram of tissue) in the peripheral RPE/choroid/sclera (circles) and central RPE/choroid/sclera (squares) over time following SCS injection of BCX4161 (0.5 mg/eye). Results are shown as the mean±the standard error of the mean (SEM); n=4 at each time point unless otherwise noted.

Methods and drug compositions are provided herein for treatment of ocular diseases and conditions, particularly posterior ocular diseases and conditions, in subjects in need of such treatment.

The treatment methods described herein are particularly useful for the local delivery of drugs to the posterior segment of the eye, such as, but not limited to, the retinochoroidal tissue, macula, retinal pigment epithelium (RPE), and optic nerve in the posterior segment of the eye. The novel drug compositions described herein provide for favorable PK parameters that result in high concentrations of a compound of the disclosure being maintained in the SCS or an ocular tissue for an extended period of time (i.e., months). The non-surgical ocular drug delivery methods provided herein can be used to target drug delivery to specific ocular tissues or regions within the posterior segment of the eye or in neighboring tissue. For example, the non-surgical ocular drug delivery methods described herein can be used to target drug delivery specifically to the sclera, the choroid, the Bruch's membrane, the retinal pigment epithelium, the subretinal space, the retina, the macula, the optic disk, the optic nerve, the ciliary body, the trabecular meshwork, and/or other ocular tissue in the posterior segment of the eye or neighboring tissue in the eye of a human subject. The methods provided herein, in one embodiment, can be used to target drug delivery to specific posterior ocular tissues or regions within the eye or in neighboring tissue.

Those skilled in the art will appreciate that the suprachoroidal space frequently is expanded by fluid buildup because of some disease state in the eye or as a result of some trauma or surgical intervention. In the present description, however, the fluid buildup is intentionally created by infusion of a drug composition into the suprachoroid to create the suprachoroidal space (which is filled with a drug composition described herein). Not wishing to be bound by theory, it is believed that the SCS region serves as a pathway for uveoscleral outflow (i.e., a natural process of the eye moving fluid from one region of the eye to the other) and becomes a real space in instances of choroidal detachment from the sclera and when a drug composition is administered as described herein.

The compounds of the disclosure provide for favorable PK parameters when administered by the non-surgical ocular drug delivery methods described herein. Such favorable PK parameters include, but are not limited to, high concentrations (such as over a minimum therapeutic amount) of the drug in the posterior segment of the eye over a period of months. As a result, subjects suffering from an ocular disease or condition as described herein can be more effectively treated using the methods and compositions of the present disclosure as compared to the treatment methods of the prior art. In addition, the increased treatment efficacy is accompanied by a reduction in the number of treatments required to achieve the superior treatment efficacy and/or a reduction in the concentration of the drug required to achieve the superior treatment efficacy.

As such the present disclosure addresses known problems in the art and provides for superior treatment methods as disclosed herein.

Definitions

The articles "a" and "an" are used herein to refer to one or to more than one (i.e., to at least one) of the grammatical object of the article. By way of example, "an element" means one element or more than one element.

As used herein, the term "anterior segment of the eye" or "anterior region of the eye" refers to the front third of the eye and the structures in front of the vitreous membrane, including the lens, cornea, iris, and the ciliary body.

As used herein, the term "antibody" refers broadly to any immunologic binding agent such as, but not limited to, IgG, IgM, IgA, IgD and IgE. An antibody can be monoclonal or polyclonal, and in one embodiment, is a humanized antibody. The term antibody is also used to refer to any antibody-like molecule that has an antigen binding region, including, but not limited to, antibody fragments such as Fab', Fab, F(ab')2, single domain antibodies, Fv, scFv (single chain Fv), and engineered multivalent antibody fragments such as dibodies, tribodies and multibodies. The techniques for preparing and using various antibody-based constructs and fragments are well known in the art (see, e.g., Antibodies: A Laboratory Manual, Cold Spring Harbor Laboratory, 1988; incorporated herein by reference).

As used herein, the term "compound(s) of the disclosure" refers to a plasma kallikrein inhibitor. In a specific embodiment, the term refers to a plasma kallikrein inhibitor disclosed herein. Preferred compounds of the disclosure are plasma kallikrein inhibitor of the formula I and/or IB, including but not limited to, BCX-4161. A compound of the disclosure may be present in any pharmaceutically acceptable form.

As used herein, the term "control composition" refers to a composition having an equivalent quantity of a compound of the disclosure in the same or equivalent formulation.

As used herein, the term "dosing interval" means the period of time in between administered doses. In certain embodiments, the dosing interval is every month, every 2 months, every 3 months, every 4 months, every 5 months, every 6 months, or up to every 12 months. In a preferred embodiment, the dosing interval is equal to or greater than every 3 months, every 4 months, or every 6 months. When a concentration or other characteristic is discussed in relation to a dosing interval, the concentration/characteristic may be determined with respect to the entire dosing interval or a specified point in the dosing interval (for example, the end of the dosing interval).

As used herein, the term "drug composition" refers to a formulation comprising a compound of the disclosure, which typically includes a pharmaceutically acceptable excipient and/or a carrier; in preferred embodiment, the drug composition contains an effective amount of a compound of the disclosure.

As used herein, the term an "effective amount," "sufficient amount" or "therapeutically effective amount" refers to an amount of a compound of the disclosure that is sufficient to provide a therapeutic benefit or desired result, including clinical results. As such, the effective amount may be sufficient, for example, treat an ocular disease or condition described herein. In certain embodiments, an effective amount is an amount of the compound of the disclosure that avoids or substantially attenuates undesirable side effects.

As used herein, the term "excipient" refers to any non-active ingredient of the formulation intended to facilitate handling, stability, dispersibility, wettability, pharmacokinetics, and/or injection of a compound of the disclosure. In one embodiment, the excipient may include, comprise of, or consist of water or saline.

As used herein, the term "exposure" refers to the concentration of a compound of the disclosure in the SCS or an ocular tissue in a subject as measured over a period of time. The exposure of a subject to a compound of the disclosure can be measured by administering a composition of the disclosure to a subject in an appropriate form, withdrawing samples at predetermined times, and measuring the amount of the compound of the disclosure in the sample using an appropriate analytical technique, such as, but not limited to, liquid chromatography. The amount of a compound of the disclosure in the sample at a certain time is determined, and the concentration and time data from all the samples are plotted to provide a curve. The area under this curve is calculated and affords the exposure of the subject to the compound of the disclosure. The terms "exposure," "area under the curve," and "area under the concentration/time curve" are intended to have the same meaning and may be used interchangeably throughout.

As used herein, the term "hollow" refers to an open pathway (i.e., a bore) through or within a puncture member of a delivery device disclosed herein, such as a microneedle.

The term includes a single, straight bore through the center of a puncture member, as well as multiple bores through the center of a puncture member, bores that follow complex paths through the puncture member, multiple entry and exit points from the bore(s), and intersecting or networks of bores. Therefore, in some embodiments, a hollow puncture member has a structure that includes one or more continuous pathways from the base portion of the puncture member to an exit point (opening) in the shaft and/or the tip portion of the puncture member distal to the base portion.

As used herein, the term "in need of treatment" refers to a judgment made by a healthcare professional that a subject requires or will benefit from treatment with a compound of the disclosure. This judgment is made based on a variety of factors that are in the realm of a healthcare professional's expertise, such as, but not limited to, the knowledge that the subject is ill, or will be ill, as the result of a disease or condition that is treatable by a method or drug composition of the disclosure.

As used herein, the term "microneedle" refers to a conduit body having a base, a shaft, and a tip end suitable for insertion into the sclera and other ocular tissue and has dimensions suitable for minimally invasive insertion and drug composition infusion as described herein. In preferred embodiments, the microneedles is a hallow microneedle. A suitable microneedle is described in WO2017/192565, WO2014/179698, WO2014/074823, WO2011/139713, WO2007/131050, and WO2007/004874.

As used herein, the term "microparticle" refers to a particle having a number average diameter of 1 to 100 μm, most preferably 1 to 25 μm and includes microspheres, microcapsules, microbubbles, and beads. Microparticles may or may not be spherical in shape.

As used herein, the term "microcapsules" refers microparticles having an outer shell surrounding a core of another material. The core can be liquid, gel, solid, gas, or a combination thereof.

As used herein, the term "microbubble" refers to a microcapsule having an outer shell surrounding a core of gas, wherein the drug is disposed on the surface of the outer shell, in the outer shell itself, or in the core. Microbubbles may respond to acoustic vibrations as known in the art for diagnosis and/or can be used to burst the microbubble to release its payload at/into a select ocular tissue site.

As used herein, the term "microspheres" refers to a spherical microparticle that comprises a shell and an optionally matrix material inside the shell. The microsphere that may be solid or porous. A porous microsphere may include a sponge-like or honeycomb structure formed by pores or voids in a matrix material or shell or may include multiple discrete voids in the matrix material or shell. The shell or matrix material may be a polymer, amino acid, saccharide, or other material known in the art.

As used herein, the term "minimum therapeutic level" means the concentration of a compound of the disclosure required to be present in a use environment (for example, the SCS or an ocular tissue, particularly a posterior ocular tissue) to provide effective treatment of a disease or condition. Such "minimum therapeutic level" may vary depending on conditions intrinsic to the subject, such as, but not limited to, the presence of co-presenting disease or condition, the concurrent use of other medications, steroid hormone levels, environmental stimuli to which the subject is exposed and/or the lifestyle of the subject. Therefore, the minimum therapeutic level may vary between subjects and/or for a given subject may vary over time. However, in general for subject being treated with a compound of the disclosure for a disease or condition described herein, the minimum therapeutic level is generally in the range of between 20 ng/ml and 60 ng/ml. In one embodiment, the minimum therapeutic level is up to about 40 ng/ml, about 50 ng/ml, or about 55 ng/ml. However, the minimum therapeutic level may be as low as about 20 ng/ml to about 30 ng/ml or may be as high about 60 ng/ml or about 70 ng/ml. When no other value is specified, the "minimum therapeutic level" of a compound of the disclosure for treatment of a disease or condition described herein is defined to be greater than or equal to 30 ng/ml and less than 70 ng/ml.

As used herein, the term "nanoparticles" are particles comprising a shell and an optional matrix material inside the shell and having a number average diameter of 1 to 1000 nm. A porous nanoparticle may include a sponge-like or honeycomb structure formed by pores or voids in a matrix material or shell or may include multiple discrete voids in the matrix material or shell. The shell or matrix material may be a polymer, amino acid, saccharide, or other material known in the art. Nanoparticles may or may not be spherical in shape.

As used herein, the term "non-Newtonian fluid" refers to a fluid that does not follow Newton's law of viscosity, i.e., constant viscosity independent of stress. In non-Newtonian fluids, viscosity can change when under force to either exhibit decreased viscosity (shear-thinning fluids) or exhibit increased viscosity (shear-thickening fluids).

As used herein, the term "non-surgical" ocular drug delivery methods refer to methods of drug delivery that do not require general anesthesia and/or retrobulbar anesthesia (also referred to as a retrobulbar block). In certain embodiments, a "non-surgical" ocular drug delivery method is performed with a puncture member having a diameter of 28 gauge or smaller. In certain embodiments, "non-surgical" ocular drug delivery methods do not require a guidance mechanism that is typically required for ocular drug delivery via a shunt or cannula.

As used herein, the term "pharmaceutically acceptable" refers to a compound that is compatible with the other ingredients of a composition and not deleterious to the subject receiving the compound or composition. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "pharmaceutically acceptable form" is meant to include known forms of a compound that may be administered to a subject, including, but not limited to, solvates, hydrates, prodrugs, isomorphs, polymorphs, pseudomorphs, neutral forms and salt forms of a compound.

As used herein, the term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids. Pharmaceutically acceptable salt forms may also include forms wherein the ratio of molecules comprising the salt is not 1:1. For example, the salt may comprise more than one inorganic or organic acid molecule per molecule of base, such as two hydrochloric acid molecules per molecule of compound of the disclosure. As another example, the salt may comprise less than one inorganic or organic acid molecule per molecule of base, such as two molecules of compound of the disclosure per molecule of tartaric acid. Salts may also exist as solvates or hydrates.

As used herein, the term "posterior segment of the eye" "posterior region of the eye" refers to the back two-thirds of the eye that includes the vitreous membrane and the structures behind it. Therefore, "posterior tissues of the eye" include, but are not limited to, the sclera, the choroid, the Bruch's membrane, the retinal pigment epithelium, the subretinal space, the retina, the macula, the optic disk, and the optic nerve; in certain embodiments, "posterior tissues of the eye" excludes the vitreous humor (such as when referring to a high concentration of a compound of the disclosure in a posterior ocular tissue). For the purpose of this disclosure, the term also optionally includes the ciliary body, the trabecular meshwork, and/or the limbus as these tissues are located adjacent to the SCS and may be exposed to a compound of the disclosure when administered as described herein.

As used herein, the term "subject" or "patient" includes all members of the animal kingdom including, but not limited to, mammals, animals (e.g., cats, dogs, horses, swine, etc.) and humans. In certain embodiments, the subject is a human.

As used herein, the term "substantially all" means at least 80% or more, such as 80%, 85%, 90% or 95% or more of the recited time period.

As used herein, the term "suprachoroidal space," "SCS," "suprachoroid," or "suprachoroidia" means the potential space in the region of the eye disposed between the sclera and choroid. This region primarily is composed of closely packed layers of long pigmented processes derived from each of the two adjacent tissues; however, a space can develop in this region as a result of fluid infusion or other material buildup in the suprachoroidal space and the adjacent tissues.

As used herein, the term "supraciliary space," means the most anterior portion of the suprachoroidal space adjacent to the ciliary body, trabecular meshwork, and limbus.

As used herein, the terms "therapeutic benefit", "therapeutic response" or "therapeutic effect" refer to a reduction in the severity of a symptom/clinical manifestation of the ocular disease or condition for which the patient is undergoing treatment, or a reduction in number of symptom(s)/ clinical manifestation(s) of the ocular disease or condition for which the patient is undergoing treatment. A complete reduction severity and/or number of clinical symptoms is not required for a therapeutic benefit, therapeutic response or a therapeutic effect to be recognized. In certain embodiments, a reduction in severity of a symptom/clinical manifestation may be by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 99%. In certain embodiments, a reduction in the number of symptoms(s)/clinical manifestation(s) may mean a reduction by 1, 2, 3, 4, 5, 6, 7, 8, 9, or 10 or more symptom(s)/clinical manifestation(s) or a reduction of all symptom(s)/clinical manifestation(s).

As used herein, the terms "treating" or "treat" refer to improving a symptom of a disease or condition and may comprise curing the disease or condition, substantially preventing the onset of the disease or condition, improving the subject's condition, alleviating one or more symptom or substantially all the symptoms resulting from the disease or condition, or curing the particular disease or condition.

As used herein, the term "alkyl" is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., C1-C10 for straight chain, C3-C30 for branched chain), and alternatively, about 20 or fewer. In one embodiment, the term "alkyl" refers to a C1-C10 straight-chain alkyl group. In one embodiment, the term "alkyl" refers to a C1-C6 straight-chain alkyl group. In one embodiment, the term "alkyl" refers to a C3-C12 branched-chain alkyl group. In one embodiment, the term "alkyl" refers to a C3-C8 branched-chain alkyl group. In one embodiment, the term "alkyl" refers to a cycloalkyl having from about 3 to about 10 carbon atoms in th ring structure, and alternatively about 3 to 6 carbons in the ring structure.

As used herein, the term "alkenyl" refers to a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1 -heptenyl, and 3-decenyl.

As used herein, the term "alkynyl" refers to a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

As used herein, the term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

As used herein, the term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

As used herein, the term "aryl" is a term of art and as used herein refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulflhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In one embodiment, the term "aryl" refers to a phenyl group.

As used herein, the term "arylalkyl" is a term of art and as used herein refers to an alkyl group substituted with an aryl group.

As used herein, the term "amino" is a term of art and as used herein refers to both unsubstituted and substituted amines, e.g., a moiety that may be represented by the general formulas:

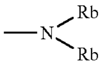
and
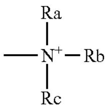

wherein $R_a$, $R_b$ and $R_c$ each independently represent a hydrogen, an alkyl, an alkenyl, —$(CH_2)_x$— $R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$. In one embodiment, the term "amino" refers to —$NH_2$.

As used herein, the term "aminoalkyl" refers to an alkyl group substituted with one or more amino groups. In one embodiment, the term "aminoalkyl" refers to an aminomethyl group.

As used herein, the term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "(cycloalkyl)alkyl" refers to an alkyl group substituted with one or more cycloalkyl groups. An example of (cycloalkyl)alkyl is a cyclopropylmethyl group.

As used herein, the term "halo" is a term of art and as used herein refers to —F, —Cl, —Br, or —I.

As used herein, the term "(heterocyclyl)alkyl" refers to an alkyl group substituted with one or more heterocyclyl groups.

As used herein, the term "heterocyclyl" refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this disclosure, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

As used herein, the term "heteroaryl" is a term of art and as used herein refers to a monocyclic, bicyclic, and polycyclic aromatic group having one or more heteroatoms in the ring structure, for example, pyrrole, furan, thiophene, imidazole, oxazole, thiazole, triazole, pyrazole, pyridine, pyrazine, pyridazine and pyrimidine, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflurom-ethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

As used herein, the term "heteroaralkyl" or "heteroarylalkyl" is a term of art and as used herein refers to an alkyl group substituted with a heteroaryl group.

As used herein, the term "phosphoryl" is a term of art and as used herein may in general be represented by the formula:

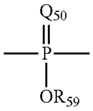

wherein $Q_{50}$ represents S or O, and $R_{59}$ represents hydrogen, a lower alkyl or an aryl; for example, —P(O)(OMe)- or —$P(O)(OH)_2$. When used to substitute, e.g., an alkyl, the phosphoryl group of the phosphorylalkyl may be represented by the general formulas:

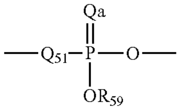
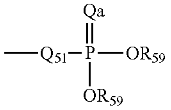

wherein $Q_{50}$ and $R_{59}$, each independently, are defined above, and $Q_{51}$ represents O, S, or N; for example, —O—P(O)(OH)OMe or —NH—$P(O)(OH)_2$. When $Q_{50}$ is S, the phosphoryl moiety is a "phosphorothioate."

It will be understood that "substitution", "substituted" or "substituted with" includes the implicit proviso that such substitution is in accordance with the permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds.

In certain embodiments, the optional substituents contemplated in this disclosure include halogen, azide, alkyl, alkenyl, alkynyl, aryl, arylalkyl, heteroaryl, heteroarylalkyl, cycloalkyl, (cycloalkyl)alkyl, heterocyclyl, (heterocyclyl) alkyl, hydroxyl, alkoxyl, amino, aminoalkyl, nitro, sulfhydryl, imino, amido, phosphonate, phosphinate, carbonyl, carboxyl, silyl, ether (e.g., -alkylene-O(alkyl)), alkylthio, sulfonyl, sulfonamido, ketone (e.g., —CO(alkyl)), aldehyde (—C(O)H), ester (e.g., —COO(alkyl)), haloalkyl, hydroxyalkyl, alkoxyalkyl, haloalkoxy, haloalkoxyalkyl, and cyano.

As used herein, the term "optionally substituted" or "substituted or unsubstituted" when it precedes a list of chemical moieties means that the list of chemical moieties that follow are each substituted or unsubstituted. For example, "substituted or unsubstituted aryl, heteroaryl, and cycloalkyl" or "optionally substituted aryl, heteroaryl, and cycloalkyl" means substituted or unsubstituted aryl, substituted or unsubstituted heteroaryl, and substituted or unsubstituted cycloalkyl.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this disclosure pertains.

Compounds of the Disclosure

The compounds of the disclosure are plasma kallikrein inhibitors. Plasma kallikrein inhibitors include small molecule inhibitors (e.g., BCX4161, BCX7353, KDV001, KDV818, KDV824, and KDV900). Plasma kallikrein inhibitors also include inhibitory peptides (such, as, but not limited to, ecallantide) and anti-plasma kallikrein antibodies (such as, but not limited to, DX-2930; lanadelumab) and fragments thereof.

In one embodiment, a compound of the disclosure is a compound of the general formula I, or a pharmaceutically acceptable form thereof:

I

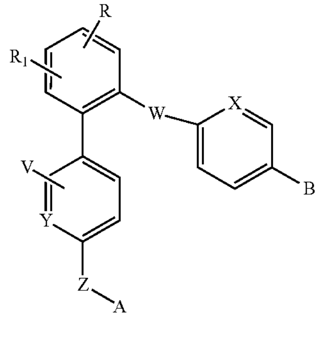

wherein:

X is CH or N;

Y is CH or N;

A is —H, —R, —$NO_2$, —CN, -halo, —$N_3$, —$C_{1-8}$ alkyl, —$(CH_2)_nCO_2R^2$, —$C_{2-8}$ alkenyl-$CO_2R^2$, —$O(CH_2)_nCO_2R^2$, —$C(O)NR^2R^3$, —C(O)NH—$(CH_2)_n$-cycloalkyl, —C(O)NH-alkyl, —$C(O)NR^2$—$C_1$-$C_5$ alkyl, —$C(O)NR^2$—$(CH_2)_n$—$C_3$-$C_6$-cycloalkyl, —$P(O)(OR^2)_2$, —$(CH_2)_nO(CH_2)_n$ aryl, —$NR^2R^3$, —$(CH_2)_nOR^2$, —$(CH_2)_nSR^2$, —$N(R^2)C(O)R^3$, —$S(O_2)NR^2R^3$, —$N(R^2)S(O_2)R^3$, —$(CHR^2)_n NR^2R^3$, —$C(O)R^3$, —$(CH_2)_nN(R^3)C(O)R^3$, —$N(R^2)CR^2R^3$ or substituted or unsubstituted $(CH_2)_n$-cycloalkyl;

B is H, -halo, —CN, —$NH_2$, —$(CH_2)_n$—$C(=NR^4)NHR^5$, —$C(=NH)NH_2$, —$(CH_2)_n$—$NHR^4$, —$(CH_2)_nNHC(=NR^4)NR^5$, —$(CH_2)n$-$OR^4$, $C_{1-8}$ substituted or $C_{1-8}$ unsubstituted alkyl;

Z is a direct bond, O, S, $NR^2$, S(O), $S(O_2)$, or N(O) containing one or two $C_{1-4}$ substituted or unsubstituted methylene chains, or a substituted or unsubstituted $C_{1-4}$ methylene chain;

W is a direct bond, —$CHR^2$—, —CH═$CR^2$—, —$CR^2$═CH—, —$CR^2$═$CR^2$—, —C≡C—, —O—$CHR^2$—, —$CHR^2$—O—, —$N(R^2)$—C(O)—, —C(O)—$N(R^2)$—, —C(O)—NH—, —$N(R^2)$—CH—$(R^3)$—, —$CH_2$—NH—, —$CH_2$—$N(R^2)$—, —$CH(R^1)$—$N(R^2)$—, —S—$CHR^2$—, —$S(O_2)$—$N(R^2)$—, —$C(O)N(R^2)$—$(CHR^2)_n$—, —$C(R^1R^2)_n$—$NR^2$—, —$N(R^2)$—$S(O_2)$—, —$R^2C(O)NR^2$—, —$R^2NC(O)NR^2$—, —$CONR^2CO$—, —$C(=NR^2)NR^2$—, —$NR^2C(=NR^2)NR^2$—, —$NR^2O$, —N═$NCHR^2$—, or —$C(O)NR^2SO_2$—;

V is selected from $R_1$;

R is —CH═CH—$R^2$, —C≡C—$R^2$, —$C(R^2)$═$CH^2$, —CH═$CH_2$, —$C(R^2)$═$C(R^3)$, —CH═$NR^2$ or —$C(R^2)$═N—$R^3$; $R^1$ is —H, —R, —$NO_2$, —CN, -halo, —$N_3$, —$C_{1-8}$ alkyl, —$(CH_2)_nCO_2R^2$, —$C_{2-8}$ alkenyl-$CO_2R^2$, —$O(CH_2)_nCO_2R^2$, —$C(O)NR^2R^3$, —$P(O)(OR^2)_2$, —$(CH_2)_nO(CH_2)_n$ aryl, —$NR^2R^3$, —$(CH_2)_nOR^2$, —O—$C_1$-$C_4$ alkyl, —$C_{1-4}$ alkoxy, —$OCH_3$, —$(CH_2)_n$ $SR^2$, —$N(R^2)C(O)R^3$, —$S(O_2)NR^2R^3$, —$N(R^2)S(O_2)R^3$, —$(CHR^2)_n$ $NR^2R^3$, —$C(O)R^3$, —C(O)OH, —$(CH_2)_nN(R^3)C(O)R^3$, or —$N(R^2)CR^2R^3$;

$R^2$ is H, -halo, -alkyl, -haloalkyl, —$CO(CHR^1)_n$—$OR^1$, —$(CHR^1)_n$—NH—CO—$R^1$, —$(CHR^1)_n$—NH—$SO_2R^1$, —$(CHR^1)_n$—$C(O)(CHR^1)$—$NHR^1$, —$(CHR^1)_n$—$C(S)(CHR^1)$—$NHR^1$, —$(CH_2)_nO(CH_2)_nCH^3$, —$CF^3$, —$C_{2-5}$ acyl, —$(CHR^1)_nOH$, —$(CHR^1)_nCO_2R^1$, —$(CHR^1)_n$—O-alkyl, —$O(CHR^1)_n$—O—$(CH_2)_n$—O-alkyl, —$(CHR^1)_n$—S-alkyl, —$(CHR^1)_n$—S(O)-alkyl, —$(CHR^1)_n$—$S(O_2)$-alkyl, —$(CHR^1)_n$—$S(O_2)$—$NHR^3$, —$(CHR^3)_n$—$N_3$, —$(CHR^3)_nNHR^4$, 2 to 8 carbon atom alkene chain having 1 to 5 double bonds, 2 to 8 carbon atom alkyne chain having 1 to 5 triple bonds or substituted or unsubstituted-$(CHR^3)_n$-cycloalkyl which may be saturated or unsaturated;

$R^3$ is —H, —OH, —CN, substituted alkyl, —$C_{2-8}$ alkenyl, —$(CH_2)_n$-cycloalkyl, substituted or unsubstituted cycloalkyl, —$N(R^1)R^2$, or 5-6 membered saturated substituted or unsubstituted heterocyclyl ring;

$R^4$ and $R^5$ individually is H, —$(CH_2)_nOH$, —$C(O)OR^6$, —$C(O)SR^6$, —$(CH_2)_nC(O)NR^7R^8$ or —O—C(O)—O—$R^7$;

each $R^6$ is H, $R^7$, —$C(R^7)(R^8)$—$(CH_2)_n$— —O—C(O)—$R^9$, —$(CH_2)_n$—$C(R^7)(R^8)$—O—C(O)$R_9$, —$(CH_2)_n$—$C(R^7)(R^8)$—O—C(O)—O—$R^9$ or —$C(R^7)(R^8)$—$(CH_2)_n$—O—C(O)—O—$R^9$;

each $R^7$, $R^8$ and $R^9$ individually is H, alkyl, substituted alkyl, aryl, substituted aryl, alkenyl, substituted alkenyl, alkynyl, substituted alkynyl, arylalkyl, substituted arylalkyl, cycloalkyl, substituted cycloalkyl, or $CH_2CO_2$alkyl; and n is an integer from 0 to 4.

In particular embodiments, the compounds of the formula I are defined as follows:

X is CH and Y is N;
X is N and Y is CH;
W is —C(O)NH—;
W is —$CH_2$—NH—;
R is CH═$CH_2$;
$R^1$ is hydrogen;
$R^1$ is —$C_1$-$C_4$ alkoxy;
$R^1$ is —$OCH_3$;
V is C(O)$R^3$;
V is C(O)OH;
R is CH═$CH_2$, $R^1$ is H and V is C(O)OH;
R is CH═$CH_2$, $R^1$ is —$OCH_3$, and V is C(O)OH;
A is —C(O)$NR^2$—$(CH_2)_n$—$C_3$-$C_6$ cycloalkyl;
A is —C(O)NH-isobutyl;
A is —C(O)NH($CH_2$)-cyclopropyl;
B is —C(═$NR^4$)$NHR^5$; and
B is —C(═NH)$NH_2$.

In one embodiment, W is —C(O)NH—, Z is a direct bond, B is —C(═NH)$NH_2$, A is —C(O)NH-isobutyl or —C(O)NH($CH_2$)-cyclopropyl, R is CH═$CH_2$, $R^1$ is H and V is C(O)OH.

In one embodiment, W is —C(O)NH—, Z is a direct bond, B is —C(═NH)$NH_2$, A is —C(O)NH-isobutyl or —C(O)NH($CH_2$)-cyclopropyl, R is CH═$CH_2$, $R^1$ is —$OCH_3$, and V is C(O)OH.

In one embodiment, X is CH, Y is N, Z is a direct bond, W is —C(O)N($R^2$)—, $R^1$ is hydrogen or methoxy, R is CH═$CH_2$, V is C(O)$R^3$ and A is —C(O)$NR^2$—$C_1$-$C_5$ alkyl or —C(O)$NR^2(CH_2)_n$—$C_3$-$C_6$ cycloalkyl. In a particular embodiment of the foregoing, $R^1$ is H. In a particular embodiment of the foregoing, $R^1$ is methoxy.

In one embodiment, X is CH, Y is N, Z is a direct bond, W is —C(O)NH—, $R^1$ is hydrogen or methoxy, R is CH═$CH_2$, V is C(O)OH and A is —C(O)NH-isobutyl or —C(O)NH—$CH_2$-cyclopropyl. In a particular embodiment of the foregoing, $R^1$ is H. In a particular embodiment of the foregoing, $R^1$ is methoxy.

In one embodiment, X is CH, Y is N, Z is a direct bond, W is —$CH_2$NH—, $R^1$ is hydrogen or methoxy, R is CH═$CH_2$, V is C(O)$R^3$ and A is —C(O)$NR^2$—$C_1$-$C_5$ alkyl or —C(O)$NR^2(CH_2)_n$—$C_3$-$C_6$ cycloalkyl. In a particular embodiment of the foregoing, $R^1$ is H. In a particular embodiment of the foregoing, $R^1$ is methoxy.

In one embodiment, X is CH, Y is N, Z is a direct bond, W is —$CH_2$NH—, $R^1$ is hydrogen or methoxy, R is CH═$CH_2$, V is C(O)OH and A is —C(O)NH-isobutyl or —C(O)NH—$CH_2$-cyclopropyl. In a particular embodiment of the foregoing, $R^1$ is H. In a particular embodiment of the foregoing, $R^1$ is methoxy.

In one embodiment, X is N, Y is CH, Z is a direct bond, W is —C(O)N($R^2$)—, $R^1$ is hydrogen or methoxy, R is CH═$CH_2$, V is C(O)$R^3$ and A is —C(O)$NR^2$—$C_1$-$C_5$ alkyl or —C(O)$NR^2(CH_2)_n$—$C_3$-$C_6$ cycloalkyl. In a particular embodiment of the foregoing, $R^1$ is H. In a particular embodiment of the foregoing, $R^1$ is methoxy.

In one embodiment, X is N, Y is CH, Z is a direct bond, W is —C(O)NH—, $R^1$ is hydrogen or methoxy, R is CH═$CH_2$, V is C(O)OH and A is —C(O)NH-isobutyl or —C(O)NH—$CH_2$-cyclopropyl. In a particular embodiment of the foregoing, $R^1$ is H. In a particular embodiment of the foregoing, $R^1$ is methoxy.

In one embodiment, X is N, Y is CH, Z is a direct bond, W is —$CH_2$NH—, $R^1$ is hydrogen or methoxy, R is CH═$CH_2$, V is C(O)$R^3$ and A is —C(O)$NR^2$—$C_1$-$C_5$ alkyl or —C(O)$NR^2(CH_2)_n$—$C_3$-$C_6$ cycloalkyl. In a particular embodiment of the foregoing, $R^1$ is H. In a particular embodiment of the foregoing, $R^1$ is methoxy.

In one embodiment, X is N, Y is CH, Z is a direct bond, W is —$CH_2$NH—, $R^1$ is hydrogen or methoxy, R is CH═$CH_2$, V is C(O)OH and A is —C(O)NH-isobutyl or —C(O)NH—$CH_2$-cyclopropyl. In a particular embodiment of the foregoing, $R^1$ is H. In a particular embodiment of the foregoing, $R^1$ is methoxy.

In one embodiment, the compounds used in the present disclosure are compounds of formula (I), as defined above, provided that when X is N, Y is CH, Z is a direct bond, W is —C(O)NH—, $R_1$ is methoxy, V is C(O)OH, B is —C(═NH)$NH_2$ and A is —C(O)NH-alkyl, the alkyl is other than isobutyl.

In one embodiment, the compound of the disclosure is a compound of the general formula IB, or a pharmaceutically acceptable form thereof:

IB

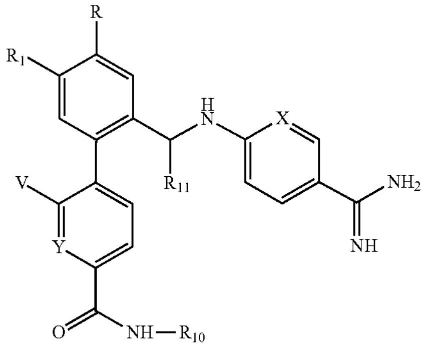

wherein

X is CH or N;

Y is CH or N;

R is —CH═CH—$R^2$, —C≡C—$R^2$, —C($R^2$)═$CH^2$, —CH═$CH_2$, —C($R^2$)═C($R^3$), —CH═$NR^2$ or —C($R^2$)═N—$R^3$;

$R^1$ is —H, —R, —$NO_2$, —CN, -halo, —$N_3$, —$C_{1-8}$ alkyl, —$(CH_2)_nCO_2R^2$, —$C_{2-8}$ alkenyl-$CO_2R^2$, —$C_{2-4}$ alkoxy, —$O(CH_2)_nCO_2R^2$, —C(O)$NR^2R^3$, —$NR^2R^3$, —$(CH_2)_nOR^2$, —C(O)OH, —O—$C_1$-$C_3$ alkyl, —$OCH_3$, N($R^2$)C(O)$R^3$, or —$(CHR^2)_n$;

V is independently selected from $R^1$;

$R^{10}$ is —$R^2R^3$, —$(CH_2)_n$-cycloalkyl, -alkyl, —$R^2$—$C_1$-$C_5$ alkyl, —$R^2$—$(CH_2)_n$—$C_3$-$C_6$-cycloalkyl, —($CH_2$)-cyclopropyl or -isobutyl;

$R^{11}$ is hydrogen or ═O; and n, $R^2$ and $R^3$ are as defined above.

Preferably, $R^{10}$ is —($CH_2$)-cyclopropyl or -isobutyl. In certain embodiments of the compounds of formula IB:

R is —CH═$CH_2$, V is —C(O)OH, Y is N, $R^{10}$ is —($CH_2$)-cyclopropyl, $R^{11}$ is ═O, X is C, and $R^1$ is —$OCH_3$.

R is —CH═CH$_2$, V is —C(O)OH, Y is N, $R^{10}$ is —(CH$_2$)-cyclopropyl, $R^{11}$ is ═O, X is C, and $R^1$ is H.

R is —CH═CH$_2$, V is —C(O)OH, Y is N, $R^{10}$ is -isobutyl, $R^{11}$ is ═O, X is C, and $R^1$ is H.

R is —CH═CH$_2$, V is —C(O)OH, Y is C, $R^{10}$ is -isobutyl, $R^{11}$ is H, X is N, and $R^1$ is H.

In some embodiments, the plasma kallikrein inhibitor is avoralstat. Avoralstat is a potent and highly specific inhibitor of human plasma kallikrein activity. The term "BCX4161" is used interchangeably with the term avoralstat herein. The chemical structure and chemical formula of avoralstat is provided below. Table 1 provides general properties of avoralstat.

BCX-4161

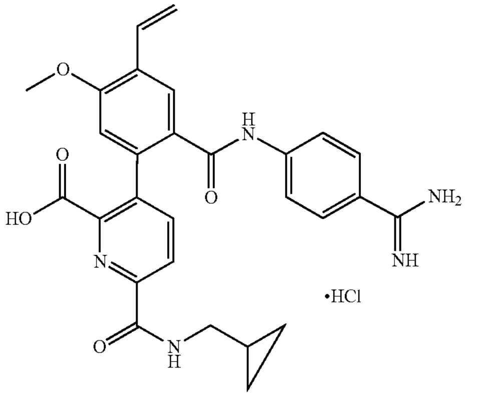

Chemical Formula: $C_{28}H_{27}N_5O_5$•HCl
Molecular Weight: 550.02

TABLE 1

| Property | Result |
|---|---|
| Appearance | White to off-white solid |
| Melting Point | Melting onset range 224-229° C. |
| Aqueous Solubility (deionized water) | About 0.02-0.04 mg/ml at room temperature (practically insoluble) |
| pH of Aqueous Saturated Solution (room temperature) | About 3.0 |
| Partition Coefficient (octanol-phosphate buffer) | log $D_{7.4}$ = 1.9 |
| p$K_a$ Values | 2.31 and 11.38 by UV-metric method |

In certain embodiments, the compounds of the disclosure, particularly a small molecule plasma kallikrein inhibitor or a compound of the formula I or IB, has an aqueous solubility in deionized water of less than or equal to 0.5 mg/ml and greater than 0.005 mg/ml, such as, but not limited to, less than or equal to 0.25 mg/ml, less than or equal to 0.2 mg/ml, less than or equal to 0.15 mg/ml, less than or equal to 0.1 mg/ml (each of the foregoing determined at room temperature). In certain embodiments, the compounds of the disclosure, particularly a small molecule plasma kallikrein inhibitor or a compound of the formula I or IB, has a log $D_{7.4}$ greater than or equal to 1.5, greater than or equal to 1.75, or greater than or equal to 2.0 (each of the foregoing in octanol phosphate buffer according to USP standard). In certain embodiments, the compounds of the disclosure, particularly a small molecule plasma kallikrein inhibitor or a compound of the formula I or IB, has an aqueous solubility in the described ranges and a log $D_{7.4}$ in the described ranges. In certain embodiment, compounds of the disclosure with reduced solubility in aqueous solutions have surprisingly been discovered to provide for the favorable PK parameters described herein, resulting in the ability to maintain high concentrations of the compounds in the disclosure in the SCS or an ocular tissue for an extended period of time (i.e., months). In any of the foregoing, the compound of the disclosure may have an $IC_{50}$ for human plasma kallikrein in the range of 0.1 to 1000 ng/ml, from 1 to 500 ng/ml or 1 to 250 ng/ml.

The effect of compounds of the disclosure on human plasma kallikrein activity is determined by the method described in Zhang et al. (Medicinal Chemistry, 2006, No. 6, p 547). Briefly, plasma kallikrein activity is determined using a chromogenic substrate (S2302). In these experiments, 2 nM plasma kallikrein (Enzyme Research Laboratories, South Bend, IN, USA) is incubated with 80 μM S2302 (H-D-Pro-Phe-Arg-p-nitroaniline) in the absence or presence of increasing concentrations of compounds of the disclosure in a final volume of 200 μL Tris-HCl buffer (200 mM NaCl; 2.5 mM $CaCl_2$; 50 mM Tris-HCl, pH 7.8). Assay reactions were initiated by adding enzyme into pre-mixed solution of inhibitors and substrate (enzyme initiated reaction) After incubation at 30° C., the activity of plasma kallikrein is measured as a change in absorbance at OD 405 nm (for example using a BioTek PowerWave X340 Microplate Reader, Winooski, VT, USA or equivalent device). Data are analyzed using appropriate software (for example, Four Parameter Logistic Curve, SigmaPlot software, Systat Software, Inc., San Jose, CA, USA or equivalent).

Any of the compounds of the disclosure may be prepared and/or administered in a pharmaceutically acceptable form. In certain embodiments, the pharmaceutically acceptable forms of a compound of the disclosure excludes prodrugs, isomorphs and/or pseudomorphs. In certain embodiments, the pharmaceutically acceptable forms of a compound of the disclosure are limited to pharmaceutically acceptable salts, neutral forms, solvates and hydrates. In certain embodiments, the pharmaceutically acceptable forms of a compound of the disclosure are limited to pharmaceutically acceptable salts and neutral forms. In certain embodiments, the pharmaceutically acceptable forms of a compound of the disclosure are limited to pharmaceutically acceptable salts.

Further, any compound of the disclosure, including the pharmaceutically acceptable forms as set forth above, may be a part of a composition, including a drug composition, either alone or in combination with a compound of the prior art. Still further, any compound of the disclosure, including the pharmaceutically acceptable forms as set forth above, may be used in any of the methods disclosed herein.

PK Parameters

As discussed herein, the drug compositions comprising a compound of the disclosure provide for favorable PK parameters when administered by the non-surgical ocular drug delivery methods described herein. As a result, the compounds of the disclosure are able to reach high concentrations in ocular tissue, particular posterior ocular tissue over a period of months. The favorable PK properties allow for a number of advantages as described herein. As a result, subjects suffering from an ocular disease or condition as described herein can be more effectively treated using the methods and compositions of the present disclosure as compared to the treatment methods of the prior art.

In one embodiment, the intraocular elimination half-life ($t_{1/2}$) of a compound of the disclosure when delivered to the SCS via the methods described herein is longer than the intraocular $t_{1/2}$ of a control composition administered intravitreally, intracamerally, topically, or systemically.

In certain aspects of this embodiment, the intraocular $t_{1/2}$ of a compound of the disclosure when administered to the SCS via the methods described herein, is up to about 1.1 times longer, up to about 2 times longer, up to about 5 times longer, up to about 10 times longer, up to about 15 times longer, up to about 20 times longer, up to about 25 times longer, up to about 30 times longer, up to about 40 times longer, or up to about 50 times longer, than the intraocular $t_{1/2}$ of a control composition administered topically, intracamerally, intravitreally, or systemically. In certain aspects of this embodiment, the intraocular $t_{1/2}$ of a compound of the disclosure when administered to the SCS via the methods described herein, is from about 1.1 times to about 50 times longer, or from about 5 times to about 50 times longer, or from about 10 times to about 50 times longer, or from about 25 times to about 50 times longer, or about 2 times to about 10 times longer, or about 2 times to about 20 times longer, or about 2 times to about 40 times longer than the intraocular $t_{1/2}$ of a control composition administered topically, intracamerally, intravitreally, or systemically.

In certain aspects of the foregoing embodiments of $t_{1/2}$, the increase in $t_{1/2}$ is observed up to about 1 week, up to about 2 weeks, up to about 3 weeks, up to about 4 weeks, up to about 2 months, up to about 3 months, up to about 4 months or longer, or up to about 4 months or longer. In certain aspects of the foregoing embodiments of $t_{1/2}$, the increase in $t_{1/2}$ is observed from about 1 week to about 6 months, from about 2 weeks to about 6 months, from about 3 weeks to about 6 months, from about 4 weeks to about 6 months, from about 2 months to about 6 months, from about 3 months to about 6 months, from about 4 months to about 6 months, or from about 5 months to about 6 months after a dose of a compound of the disclosure is administered to a subject by the methods described herein.

In one aspect of the any of the foregoing embodiments of $t_{1/2}$, the compound of the disclosure is a small molecule plasma kallikrein inhibitor, an inhibitory peptide, or an anti-plasma kallikrein antibody, or fragment thereof. In another aspect of the any of the foregoing embodiments of $t_{1/2}$, the compound of the disclosure is a compound of the formula I or a compound of the formula IB. In another aspect of the any of the foregoing embodiments of $t_{1/2}$, the compound of the disclosure is BCX4161.

In another embodiment, the intraocular $C_{max}$ of a compound of the disclosure, when delivered to the SCS via the methods described herein, is greater than the intraocular $C_{max}$ of a control composition administered intravitreally, intracamerally, topically, or systemically.

In certain aspects of this embodiment, the intraocular $C_{max}$ of compound of the disclosure when administered to the SCS via the methods described herein, is up to about 2 times greater, up to about 5 times greater, up to about 10 times greater, up to about 15 times greater, up to about 20 times greater, up to about 30 times greater, up to about 40 times greater, up to about 50 times greater, or up to about 60 times greater, than the intraocular $C_{max}$ of a control composition administered topically, intracamerally, intravitreally, or systemically. In certain aspects of this, the intraocular $C_{max}$ of compound of the disclosure when administered to the SCS via the methods described herein, is about 1.1 to about 60 times greater, or about 5 to about 60 times greater, or about 10 to about 60 times greater, or about 20 to about 60 times greater, or about 230 to about 60 times greater, or about 2 to about 10 times greater, or about 5 to about 15 times greater, or about 15 to about 30 times greater, or about 20 to about 40 times greater, or about 30 to about 60 times greater, than the intraocular $C_{max}$ of a control composition administered topically, intracamerally, intravitreally, or systemically.

In certain aspects of the foregoing embodiments of $C_{max}$, the increase in $C_{max}$ is observed up to about 1 week, up to about 2 weeks, up to about 3 weeks, up to about 4 weeks, up to about 2 months, up to about 3 months, or up to about 4 months, up to about 5 months, or up to about 6 months after a dose of a compound of the disclosure is administered to a subject by the methods described herein. In certain aspects of the foregoing embodiments of $C_{max}$, the increase in $C_{max}$ is observed from about 1 week to about 6 months, from about 2 weeks to about 6 months, from about 3 weeks to about 6 months, from about 4 weeks to about 6 months, from about 2 months to about 6 months, from about 3 months to about 6 months, from about 4 months to about 6 months, or from about 5 months to about 6 months after a dose of a compound of the disclosure is administered to a subject by the methods described herein.

In one aspect of the any of the foregoing embodiments of $C_{max}$, the compound of the disclosure is a small molecule plasma kallikrein inhibitor, an inhibitory peptide, or an anti-plasma kallikrein antibody, or fragment thereof. In another aspect of the any of the foregoing embodiments of $C_{max}$, the compound of the disclosure is a compound of the formula I or a compound of the formula IB. In another aspect of the any of the foregoing embodiments of $C_{max}$, the compound of the disclosure is BCX4161.

In another embodiment, the mean intraocular area under the curve ($AUC_{0-t}$) of a compound of the disclosure, when delivered to the SCS via the methods described herein, is greater than the intraocular $AUC_{0-t}$ of a control composition administered intravitreally, intracamerally, topically, or systemically.

In certain aspects of this embodiment, the intraocular $AUC_{0-t}$ of compound of the disclosure when administered to the SCS via the methods described herein, is up to about 1.1 times greater, or up to about 2.5 times greater, or up to about 5 times greater, or up to about 10 times greater, or up to about 15 times greater, or up to about 20 times greater, or up to about 30 times greater, or up to about 50 times greater than the intraocular $AUC_{0-t}$ of a control composition administered topically, intracamerally, intravitreally, or systemically. In certain aspects of this, the intraocular $AUC_{0-t}$ of compound of the disclosure when administered to the SCS via the methods described herein, is about 2.5 to about 50 times greater, or about 5 to about 50 times greater, or about 10 to about 50 times greater, or about 15 to about 50 times greater, or about 20 to about 50 times greater, or about 30 to about 50 times greater, or about 2 to about 10 times greater, or about 5 to about 15 times greater, or about 15 to about 30 times greater, or about 20 to about 40 times greater, or about 30 to about 50 times greater, than the intraocular $AUC_{0-t}$ of a control composition administered topically, intracamerally, intravitreally, or systemically.

In certain aspects of the foregoing embodiments of $AUC_{0-t}$, t is (i.e., the increase in $AUC_{0-t}$ is observed over a time period of 0 to t) up to about 1 week, up to about 2 weeks, up to about 3 weeks, up to about 4 weeks, up to about 2 months, up to about 3 months, up to about 4 months, up to about 5 months, or up to about 6 months.

In one aspect of the any of the foregoing embodiments of $AUC_{0-t}$, the compound of the disclosure is a small molecule plasma kallikrein inhibitor, an inhibitory peptide, or an anti-plasma kallikrein antibody, or fragment thereof. In another aspect of the any of the foregoing embodiments of $AUC_{0-t}$, the compound of the disclosure is a compound of the formula I or a compound of the formula IB. In another aspect of the any of the foregoing embodiments of $AUC_{0-t}$, the compound of the disclosure is BCX4161.

In another embodiment, the mean intraocular area under the curve over a dosing interval ($AUC_{tau}$) of a compound of the disclosure, when delivered to the SCS via the methods described herein, is greater than the intraocular $AUC_{tau}$ of a control composition administered intravitreally, intracamerally, topically, or systemically.

In certain aspects of this embodiment, the intraocular $AUC_{tau}$ of compound of the disclosure when administered to the SCS via the methods described herein, is up to about 1.1 times greater, or up to about 2.5 times greater, or up to about 5 times greater, or up to about 10 times greater, or up to about 15 times greater, or up to about 20 times greater, or up to about 30 times greater, or up to about 50 times greater than the intraocular $AUC_{tau}$ of a control composition administered topically, intracamerally, intravitreally, or systemically. In certain aspects of this embodiment, the intraocular $AUC_{tau}$ of compound of the disclosure when administered to the SCS via the methods described herein, is about 2.5 to about 50 times greater, or about 5 to about 50 times greater, or about 10 to about 50 times greater, or about 15 to about 50 times greater, or about 20 to about 50 times greater, or about 30 to about 50 times greater, or about 2 to about 10 times greater, or about 5 to about 15 times greater, or about 15 to about 30 times greater, or about 20 to about 40 times greater, or about 30 to about 50 times greater, than the intraocular $AUC_{tau}$ of a control composition administered topically, intracamerally, intravitreally, or systemically.

In certain aspects of the foregoing embodiments of $AUC_{tau}$, the dosing interval is about every 1 week, about every 2 weeks, about every 3 weeks, about every 4 weeks, about every 2 months, about every 3 months, about every 4 months, about every 5 months, or about every 6 months.

In one aspect of the any of the foregoing embodiments of $AUC_{tau}$, the compound of the disclosure is a small molecule plasma kallikrein inhibitor, an inhibitory peptide, or an anti-plasma kallikrein antibody, or fragment thereof. In another aspect of the any of the foregoing embodiments of $AUC_{tau}$, the compound of the disclosure is a compound of the formula I or a compound of the formula IB. In another aspect of the any of the foregoing embodiments of $AUC_{tau}$, the compound of the disclosure is BCX4161.

In another embodiment, the time to maximum concentration ($T_{max}$) of a compound of the disclosure, when delivered to the SCS via the methods described herein, is delayed as compared to the $T_{max}$ of a control composition administered intravitreally, intracamerally, topically, or systemically, and the $AUC_{0-t}$ or $AUC_{tau}$ of the compound of the disclosure is greater than the $AUC_{0-t}$ or $AUC_{tau}$ of the control composition administered intravitreally, intracamerally, topically, or systemically.

In certain aspects of this embodiment, the time to $T_{max}$ is delayed from about 2 times to about 20 times as compared to a control composition administered topically, intracamerally, intravitreally, or systemically and optionally the $AUC_{0-t}$ or $AUC_{tau}$ of compound of the disclosure when administered to the SCS via the methods described herein, is up to about 1.1 times greater, or up to about 2.5 times greater, or up to about 5 times greater, or up to about 10 times greater, or up to about 15 times greater, or up to about 20 times greater, or up to about 30 times greater, or up to about 50 times greater than the intraocular $AUC_{0-t}$ or $AUC_{tau}$ of a control composition administered topically, intracamerally, intravitreally, or systemically. In certain aspects of this embodiment, the time to $T_{max}$ is delayed from about 2 times to about 20 times as compared to a control composition administered topically, intracamerally, intravitreally, or systemically and the intraocular $AUC_{tau}$ of compound of the disclosure when administered to the SCS via the methods described herein, is about 2.5 to about 50 times greater, or about 5 to about 50 times greater, or about 10 to about 50 times greater, or about 15 to about 50 times greater, or about 20 to about 50 times greater, or about 30 to about 50 times greater, or about 2 to about 10 times greater, or about 5 to about 15 times greater, or about 15 to about 30 times greater, or about 20 to about 40 times greater, or about 30 to about 50 times greater, than the intraocular $AUC_{0-t}$ or $AUC_{tau}$ of a control composition administered topically, intracamerally, intravitreally, or systemically.

In certain aspects of the foregoing embodiments of $AUC_{tau}$, the dosing interval is about every 1 week, about every 2 weeks, about every 3 weeks, about every 4 weeks, about every 2 months, about every 3 months, about every 4 months, about every 5 months, or about every 6 months.

In certain aspects of the foregoing embodiments of $AUC_{0-t}$, t is (i.e., the increase in $AUC_{0-t}$ is observed over a time period of 0 to t) up to about 1 week, up to about 2 weeks, up to about 3 weeks, up to about 4 weeks, up to about 2 months, up to about 3 months, up to about 4 months, up to about 5 months, or up to about 6 months.

In one aspect of the any of the foregoing embodiments of $T_{max}$, the compound of the disclosure is a small molecule plasma kallikrein inhibitor, an inhibitory peptide, or an anti-plasma kallikrein antibody, or fragment thereof. In another aspect of the any of the foregoing embodiments of $T_{max}$, the compound of the disclosure is a compound of the formula I or a compound of the formula IB. In another aspect of the any of the foregoing embodiments of $T_{max}$, the compound of the disclosure is BCX4161.

In another embodiment, administration of a drug compositions comprising a compound of the disclosure to the SCS via the methods described herein provides a dosing interval of from 1 to 12 months. For example, the dosing interval may be 1 month, 2 months, 3 months, 4 months, 5 months, 6 months or up to 12 months. Preferably, the dosing interval is from 3 months to 6 months.

In another embodiment, administration of a compound of the disclosure to the SCS via the methods described herein provides a dosing interval of from 1 to 12 months, wherein the concentration of the compound of the disclosure in the SCS or an ocular tissue is above a minimum therapeutic level over all or substantially all of the dosing interval. For example, the dosing interval may be 1 month, 2 months, 3 months, 4 months, 5 months, 6 months or 12 months. Preferably, the dosing interval is from 3 months to 6 months. In certain aspects of this embodiment, the minimum therapeutic concentration is from about 20 ng/ml to about 60 ng/ml, from about 30 to about 55 ng/ml, or from about 40 ng/ml to about 50 ng/ml.

In one aspect of the any of the foregoing embodiments regarding the dosing interval, the compound of the disclosure is a small molecule plasma kallikrein inhibitor, an inhibitory peptide, or an anti-plasma kallikrein antibody, or fragment thereof. In another aspect of the any of the foregoing embodiments regarding the dosing interval, the compound of the disclosure is a compound of the formula I or a compound of the formula IB. In another aspect of the any of the foregoing embodiments regarding the dosing interval, the compound of the disclosure is BCX4161.

In another embodiment, administration of a drug compositions comprising a compound of the disclosure to the SCS via the methods described herein provides a concentration of the compound of the disclosure that is above a minimum therapeutic level in the SCS or an ocular tissue for up to about 1 month after administration, up to about 2 months after administration, up to about 3 months after administration, up to about 4 months after administration, up to about 5 months after administration, up to about 6 months, or up to about 12 months after administration. Preferably, the concentration of the compound of the disclosure is above the minimum therapeutic level in the SCS or an ocular tissue for at least 3 months to 6 months. In certain aspects of this embodiment, the minimum therapeutic concentration is from about 20 ng/ml to about 60 ng/ml, from about 30 to about 55 ng/ml, or from about 40 ng/ml to about 50 ng/ml. In certain aspects of this embodiment, the ocular tissue is the sclera, the choroid, the Bruch's membrane, the RPE, the subretinal space, the retina, the macula, the optic disk, the optic nerve, the ciliary body, and/or the trabecular meshwork. In certain aspects of this embodiment, the ocular tissue is the ocular tissue is the sclera, the choroid, the Bruch's membrane, the RPE, the retina, the macula, the peripheral RPE, peripheral choroid, peripheral sclera, the peripheral retina, the central RPE, central choroid, central sclera, and/or the central retina.

In another embodiment, administration of a drug compositions comprising a compound of the disclosure to the SCS via the methods described herein provides a concentration of the compound of the disclosure that is above 30 ng/ml in the SCS or an ocular tissue for up to about 1 month after administration, up to about 2 months after administration, up to about 3 months after administration, up to about 4 months after administration, up to about 5 months after administration, up to about 6 months, or up to about 12 months after administration. Preferably, the concentration of the compound of the disclosure is above 30 ng/ml in the SCS or an ocular tissue for at least 3 months to 6 months. In certain aspects of this embodiment, the ocular tissue is the sclera, the choroid, the Bruch's membrane, the RPE, the subretinal space, the retina, the macula, the optic disk, the optic nerve, the ciliary body, and/or the trabecular meshwork. In certain aspects of this embodiment, the ocular tissue is the ocular tissue is the sclera, the choroid, the Bruch's membrane, the RPE, the retina, the macula, the peripheral RPE, peripheral choroid, peripheral sclera, the peripheral retina, the central RPE, central choroid, central sclera, and/or the central retina.

In another embodiment, administration of a drug compositions comprising a compound of the disclosure to the SCS via the methods described herein provides a concentration of the compound of the disclosure that is above 40 ng/ml in the SCS or an ocular tissue for up to about 1 month after administration, up to about 2 months after administration, up to about 3 months after administration, up to about 4 months after administration, up to about 5 months after administration, up to about 6 months, or up to about 12 months after administration. Preferably, the concentration of the compound of the disclosure is above 40 ng/ml in the SCS or the ocular tissue for at least 3 months to 6 months. In certain aspects of this embodiment, the ocular tissue is the sclera, the choroid, the Bruch's membrane, the RPE, the subretinal space, the retina, the macula, the optic disk, the optic nerve, the ciliary body, and/or the trabecular meshwork. In certain aspects of this embodiment, the ocular tissue is the ocular tissue is the sclera, the choroid, the Bruch's membrane, the RPE, the retina, the macula, the peripheral RPE, peripheral choroid, peripheral sclera, the peripheral retina, the central RPE, central choroid, central sclera, and/or the central retina.

In another embodiment, administration of a drug compositions comprising a compound of the disclosure to the SCS via the methods described herein provides a concentration of the compound of the disclosure that is above 50 ng/ml in the SCS or an ocular tissue for up to about 1 month after administration, up to about 2 months after administration, up to about 3 months after administration, up to about 4 months after administration, up to about 5 months after administration, up to about 6 months, or up to about 12 months after administration. Preferably, the concentration of the compound of the disclosure is above 50 ng/ml in the SCS or the ocular tissue for at least 3 months to 6 months. In certain aspects of this embodiment, the ocular tissue is the sclera, the choroid, the Bruch's membrane, the RPE, the subretinal space, the retina, the macula, the optic disk, the optic nerve, the ciliary body, and/or the trabecular meshwork. In certain aspects of this embodiment, the ocular tissue is the ocular tissue is the sclera, the choroid, the Bruch's membrane, the RPE, the retina, the macula, the peripheral RPE, peripheral choroid, peripheral sclera, the peripheral retina, the central RPE, central choroid, central sclera, and/or the central retina.

In another embodiment, administration of a drug compositions comprising a compound of the disclosure to the SCS via the methods described herein provides a concentration of the compound of the disclosure that is above 100 ng/ml in the SCS or an ocular tissue for up to about 1 month after administration, up to about 2 months after administration, up to about 3 months after administration, up to about 4 months after administration, up to about 5 months after administration, up to about 6 months, or up to about 12 months after administration. Preferably, the concentration of the compound of the disclosure is above 100 ng/ml in the SCS or the ocular tissue for at least 3 months to 6 months. In certain aspects of this embodiment, the ocular tissue is the sclera, the choroid, the Bruch's membrane, the RPE, the subretinal space, the retina, the macula, the optic disk, the optic nerve, the ciliary body, and/or the trabecular meshwork. In certain aspects of this embodiment, the ocular tissue is the ocular tissue is the sclera, the choroid, the Bruch's membrane, the RPE, the retina, the macula, the peripheral RPE, peripheral choroid, peripheral sclera, the peripheral retina, the central RPE, central choroid, central sclera, and/or the central retina.

In another embodiment, administration of a compound of the disclosure to the SCS via the methods described herein provides a concentration of the compound of the disclosure that is above 250 ng/ml in the SCS or an ocular tissue for up to about 1 month after administration, up to about 2 months after administration, up to about 3 months after administration, up to about 4 months after administration, up to about 5 months after administration, up to about 6 months, or up to about 12 months after administration. Preferably, the concentration of the compound of the disclosure is above 250 ng/ml in the SCS or the ocular tissue for at least 3 months to 6 months. In certain aspects of this embodiment, the ocular tissue is the sclera, the choroid, the Bruch's membrane, the RPE, the subretinal space, the retina, the macula, the optic disk, the optic nerve, the ciliary body, and/or the trabecular meshwork. In certain aspects of this embodiment, the ocular tissue is the sclera, the choroid, the Bruch's membrane, the RPE, the retina, the macula, the peripheral RPE, peripheral choroid, peripheral sclera, the peripheral retina, the central RPE, central choroid, central sclera, and/or the central retina.

In one aspect of the any of the foregoing embodiments regarding the concentration of a compound of the disclosure, the compound of the disclosure is a small molecule plasma kallikrein inhibitor, an inhibitory peptide, or an anti-plasma kallikrein antibody, or fragment thereof. In another aspect of the any of the foregoing embodiments regarding the concentration of a compound of the disclosure, the compound of the disclosure is a compound of the formula I or a compound of the formula IB. In another aspect of the any of the foregoing embodiments regarding the concentration of a compound of the disclosure, the compound of the disclosure is BCX4161.

Device for Administration to the Suprachoroidal Space

A number of devices may be used to deliver a compound of the disclosure or a drug composition of the present disclosure to the SCS. Such devices may be known in the art or may be developed in the future.

In one embodiment, the device used to deliver a compound of the disclosure or a drug composition of the present disclosure to the SCS is known in the art and described in, for example, WO2017/192565, WO2014/179698, WO2014/074823, WO2011/139713, WO2007/131050, and WO2007/004874. Other suitable devices are described in U.S. Publication Nos. 2018/0256393 or 2017/0273825, U.S. Pat. No. 10,226,379 or 9,084,662.

With the SCS drug delivery methods and devices described herein (including devices that incorporate a microneedle), the methods advantageously include precise control of the depth of insertion into the ocular tissue, so that the drug composition flows into the SCS and in some embodiments to the posterior ocular tissues surrounding the SCS. In one embodiment, insertion of a puncture member is in the sclera of the eye. In one embodiment, drug flow into the SCS is accomplished without contacting underlying tissues with the microneedle, such as choroid and retina tissues.

In preferred embodiments of the present disclosure the device used to deliver a drug composition of the present disclosure to the SCS has one or more of the following features or the combination of the device and the drug formulation provide one or more of the following benefits:

1. The device provides a puncture member to deliver the drug composition to the SCS. A preferred puncture member is a microneedle, more preferably a hollow microneedle.
2. The device provides for precise control of the depth of insertion of a puncture member into the ocular tissue.
3. The device provides for administration of the drug composition to the SCS without contacting underlying tissues with the puncture member, such as choroid and retina tissues.
4. The device provides for administering and localizing the drug composition to one or more ocular tissues, particularly posterior ocular tissues, such as, but not limited to, the RPE, the macula and/or the subretinal space.
5. Delivery of the drug composition comprising a compound of the disclosure by the methods described herein provides a decreased effective amount in a drug composition as compared to the effective amount in a control composition delivered by another method, such as, but not limited to, systemic, intracameral, topical, and/or IVT.
6. Delivery of the drug composition comprising a compound of the disclosure by the methods described herein provides for an extended release of a compound of the disclosure to one or more ocular tissues as compared to a compound of the disclosure control composition administered by another method, such as, but not limited to, systemic, intracameral, topical, and/or IVT.
7. Delivery of the drug composition comprising a compound of the disclosure by the methods described herein provides for a decreased number of deleterious side effects or clinical manifestations on administration of a compound of the disclosure as compared to the number of side effects or clinical manifestations caused by the compound of the disclosure control composition administered by another method, such as, but not limited to, systemic, intracameral, topical, and/or IVT.

In some embodiments, the device provides for the delivery of a compound of the disclosure or a drug composition of the disclosure via a puncture member. Examples of a suitable puncture member include, but are not limited to, a microneedle, a needle, a trocar, a cannula, and similar structures, wherein the puncture member defines a hollow interior. In certain embodiments, the puncture member does not have an opening at a distal end portion. In a preferred embodiment, the puncture member is a microneedle. A microneedle refers to a body having a base portion, a shaft, and a tip end opposite the base portion, the tip end suitable for insertion into the ocular tissue, for example, the sclera, such that a compound of the disclosure or drug composition of the disclosure is delivered to the SCS.

In preferred embodiments, the microneedle has dimensions suitable for minimally invasive insertion into the ocular tissue and/or infusion of a compound of the disclosure or a drug composition of the disclosure. Preferred dimensions are described in WO2017/192565, WO2014/179698, WO2014/074823, WO2011/139713, WO2007/131050, and WO2007/004874. In certain embodiments, the microneedle is a 28-gauge microneedle 32-gauge microneedle or a 34-gauge microneedle. In certain embodiments, the shape and/or size of the microneedle can correspond, at least partially, with at least a portion of a target tissue. For example, in certain embodiments, the length of the microneedle can correspond with a thickness of a portion of ocular tissue such that when the microneedle is inserted into the ocular tissue, at least a portion of the microneedle is disposed within the sclera or suprachoroidal space of the eye.

In certain embodiments, the microneedle has a length or effective length that does not exceed about 2000 microns and a diameter that does not exceed about 600 microns. Both the "length" and "effective length" of the microneedle encompass the length of the shaft of the microneedle and the bevel height of the microneedle. In certain embodiments, the microneedle is a hollow microneedle. In other embodiments, other types of microneedles (for example, solid microneedles) are useful in the methods provided herein.

In one embodiment, the microneedle has an effective length of about 50 μm to about 2000 μm. In another particular embodiment, the microneedle has an effective length of from about 150 μm to about 1500 μm, or from about 300 μm to about 1250 μm, or from about 500 μm to about 1250 μm, or from about 500 μm to about 1500 μm, or from about 600 μm to about 1000 μm, or from about 700 μm to about 1000 μm. In one embodiment, the effective length of the microneedle is about 600 μm, or about 700 μm, or about 800 μm or about 1000 μm. In various embodiments, the proximal portion of the microneedle has a maximum width or cross-sectional dimension of from about 50 μm to 600 μm, or from about 50 μm to about 400 μm, or from about 50 μm to about 500 μm, or from about 100 μm to about 400 μm, or from about 200 μm to about 600 μm, or from about 100 μm to about 250 μm, with an aperture diameter of about 5 μm to about 400 μm. In a particular embodiment, the proximal portion of the microneedle has a maximum width or cross-sectional dimension of about 600 μm. Those skilled in the art will appreciate, however, that in embodiments in which the tip end of the microneedle is beveled that the aperture diameter may be greater than the outer diameter of the proximal portion of the microneedle.

The microneedle may be fabricated to have an aspect ratio (width:length) of about 1:1.5 to about 1:10. In one embodiment, the aspect ratio of the microneedle is about 1:3 to about 1:5. In another embodiment, the aspect ratio of the microneedle is about 1:4 to about 1:10.

The microneedle can have a straight or tapered shaft. In one embodiment, the diameter of the microneedle is greatest at the base portion of the microneedle and tapers to a point at the tip end distal the base portion. The microneedle can also be fabricated to have a shaft that includes both a straight (i.e., untapered) portion and a tapered (e.g., beveled) portion. In various embodiments the microneedle has a bevel angle of about 5 degrees to about 30 degrees, of about 5 degrees to about 25 degrees, about 5 degrees to about 20 degrees, about 10 degrees to about 20 degrees, and about 10 degrees to about 30 degrees. The microneedles can be formed with shafts that have a circular cross-section in the perpendicular, or the cross-section can be non-circular. The tip portion of the microneedles can have a variety of configurations. The tip of the microneedle can be symmetrical or asymmetrical about the longitudinal axis of the shaft. The tips may be beveled, tapered, squared-off, or rounded. In various embodiments, the microneedle has a bevel height from about 50 μm to 500 μm, about 100 μm to about 500 μm, about 100 μm to about 400 μm, about 200 μm to about 400 μm, and about 300 μm to about 500 μm. In particular embodiments, the microneedle may be designed such that the tip portion of the microneedle is substantially the only portion of the microneedle inserted into the ocular tissue (i.e., the tip portion is greater than 75% of the total length of the microneedle, greater than 85% of the total length of the microneedle, or greater than about 95% of the total length of the microneedle). In other particular embodiments, the microneedle may be designed such that the tip portion is only a portion of the microneedle that is inserted into the ocular tissue and generally has a length that is less than about 75% of the total length of the microneedle, less than about 50% of the total length of the microneedle, or less than about 25% of the total length of the microneedle. For example, in one embodiment the microneedle has a total effective length between 500 μm and 1500 μm, wherein the tip portion has a length that is less than about 400 μm, less than about 300 μm, or less than about 200 μm.

In one embodiment, the height of the bevel is about 100 μm to about 500 μm. In another embodiment, the height of the bevel is about 500 μm or less, about 450 μm or less, about 400 μm or less or about 350 μm or less. In another embodiment, the height of the bevel is from about 200 μm to about 500 μm, or from about 100 μm to about 700 μm, or from about 200 μm to about 700 μm. In still other embodiments, the height of the bevel is from about 500 μm to about 900 μm, or from about 500 μm to about 800 μm, or from about 500 μm to about 700 μm. In this manner, the arrangement of the bevel can be such that the distal edge is sufficiently sharp such as to pierce a target tissue and penetrate into the ocular tissue without (i) substantially causing the target tissue to elastically deform or (ii) damaging internal structures of the eye, e.g., the lens or retina.

In one embodiment, the microneedle extends from a base portion. The base portion may be integral with or separate from the microneedle. The base portion may be rigid or flexible. The base portion may be substantially planar or it may be curved, for example, in the shape of the ocular tissue surface at the site of injection or, for example, curved away from the ocular surface (e.g., convex) so as to minimize contact between the base portion and the ocular tissue. Desirably, the base portion is shaped to provide minimal contact with the surface of the eye at the point of insertion. For example, in one embodiment, the base portion may extend only a minimal distance from the microneedle shaft substantially perpendicular. In another embodiment, the base portion may be shaped so as to elevate the ocular tissue towards the microneedle so as to counteract the deflection of the ocular tissue and facilitate insertion of the microneedle into the ocular tissue (e.g., the base portion may extend from the microneedle toward the tip portion of the microneedle so as to "pinch" the ocular tissue). Some such embodiments may be based, at least in part, on the devices described in U.S. Pat. No. 6,743,211.

The microneedle may extend from the base portion of the microneedle device at any angle suitable for insertion into the eye. In a particular embodiment, the microneedle extends from the base at an angle of about 90 degrees to provide approximately perpendicular insertion of the microneedle into the surface of the eye. In another particular embodiment, the microneedle extends from the base portion at an angle from about 60 to about 110 degrees, or from about 70 degrees to about 100 degrees, or from about 80 degrees to about 90 degrees, or from about 85 degrees to about 95 degrees.

The device or the microneedle device may comprise a means for controllably inserting, and optionally retracting, the microneedle into or out of the ocular tissue. In addition, the device or microneedle may include means of controlling the angle at which the microneedle is inserted into the ocular tissue. In one embodiment, the means for controlling results in the insertion of a microneedle into the surface of the ocular tissue at an angle of about 90 degrees.

The depth of microneedle insertion into the ocular tissue can be controlled by the length of the microneedle, as well as other geometric features of the microneedle. For example, a flange or other sudden change in microneedle width can be used to limit the depth of microneedle insertion. The microneedle insertion can also be controlled using a mechanical micropositioning system involving gears or other mechanical components that move the microneedle into the ocular tissue a controlled distance and, likewise, can be operated, for example, in reverse, to retract the microneedle a controlled distance. The depth of insertion can also be controlled by the velocity at which the microneedle is inserted into the ocular tissue. The retraction distance can be controlled by elastic recoil of the ocular tissue into which the microneedle is inserted or by including an elastic element within the microneedle device that pulls the microneedle back a specified distance after the force of insertion is released.

The angle of insertion can be directed by positioning the microneedle at a first angle relative to the microneedle base and positioning the base at a second angle relative to the ocular surface. In one embodiment, the first angle can be about 90° and the second angle can be about 0°. The angle of insertion can also be directed by having the microneedle protrude from a device housing through a channel in that housing that is oriented at a specified angle.

The transport of drug composition through a hollow microneedle can be controlled and/or monitored using, for example, one or more valves, pumps, sensors, actuators, and microprocessors. In one embodiment the device or microneedle may include a micropump, microvalve, and positioner, with a microprocessor programmed to control a micropump or microvalve to control the rate of delivery of the drug composition through the microneedle and into the ocular tissue. The flow through a microneedle may be driven by diffusion, capillary action, a mechanical pump, electroosmosis, electrophoresis, convection or other driving forces. Device and microneedle designs can be tailored using known pumps and other devices to utilize these drivers. In one embodiment, the microneedle device may further include an iontophoretic apparatus, similar to that described in U.S. Pat. No. 6,319,240, for enhancing the delivery of the drug composition to the ocular tissue. In another embodiment the device or microneedle can further include a flowmeter or other means to monitor flow through the microneedles and to coordinate use of the pumps and valves. In some embodiments, the transport of drug composition or biological fluid through a microneedle can be controlled or monitored using the methods and devices disclosed in WO 2014/179698, incorporated herein by reference in its entirety.

Those skilled in the art will appreciate, however, that other types of microneedles (for example, a solid microneedle) and other methods of delivering the drug composition into the suprachoroidal space may be used instead of or in conjunction with the delivery methods described herein. Non-limiting examples of such alternate methods include dissolving, at least in part, a coating of a drug composition off of a microneedle inserted into the suprachoroidal space, detaching, at least in part, a coating of a drug composition (either as a substantially intact sleeve or as one or more fragments) off of a microneedle into the suprachoroidal space, breaking or dissolving a microneedle off of a base to which the microneedle is integrally formed or is connected, or any combination thereof.

Drug Composition

The drug composition delivered by the methods described herein, in one embodiment, comprises an effective amount of a compound of the disclosure. A preferred compound of the disclosure is BCX4161. In some embodiments, the compound of the disclosure is a small molecule plasma kallikrein inhibitor. In some embodiments the compound of the disclosure is an inhibitory peptide or an anti-plasma kallikrein antibody. In various embodiments, the drug composition may be a fluid composition, a semi-solid composition, a gel composition, or a solid composition. In one embodiment, the drug composition is a fluid composition when injected and is converted to a gel composition of a semi-solid composition at or after injection into the suprachoroidal space.

A drug composition, including a liquid drug composition, may include any biocompatible liquid formulation, and may include water or an aqueous formulation including one or more salts. In some embodiments, the liquid formulation is Hank's Balanced Salt Solution HMS or another saline solution. In some embodiments, the liquid formulation is water. The volume of the liquid formulation may be any volume capable of reducing the minimum force to separate the sclera and choroid. In some embodiments, the volume of the liquid formulation is about 50 μL to about 500 μL, about 50 μL to about 275 μL, about 50 μL to about 250 μL, about 50 μL to about 225 μL, about 50 μL to about 200 μL, about 50 μL to about 175 μL, about 50 μL to about 150 μL, about 60 μL to about 140 μL, about 70 μL to about 130 μL, about 80 μL to about 120 μL, about 90 μL to about 110 μL, or about 100 μL.

In certain embodiments, the drug composition comprises an effective amount of a compound of the disclosure per administration. In certain embodiments, the effective amount of a compound of the disclosure in the drug composition ranges from about 0.01 mg to about 20 mg. In certain embodiments, the effective amount ranges from about 0.05 mg to about 15 mg. In certain embodiments, the effective amount ranges from about 0.1 mg to about 10 mg. In certain embodiments, the effective amount ranges from about 0.2 mg to about 8 mg. In certain embodiments, the effective amount ranges from about 0.3 mg to about 7 mg. In certain embodiments, the effective amount ranges from about 0.4 mg to about 6 mg. In certain embodiments, the effective amount ranges from about 0.5 mg to about 5 mg. In certain embodiments, the effective amount ranges from about 0.6 mg to about 4 mg. In certain embodiments, the effective amount ranges from about 0.7 mg to about 3 mg. In certain embodiments, the effective amount ranges from about 0.8 mg to about 2 mg. In certain embodiments, the effective amount ranges from about 0.9 mg to about 1.5 mg. In certain embodiments, the effective amount ranges from about 0.1 mg to about 3 mg. In certain embodiments, the effective amount ranges from about 0.2 mg to about 2.5 mg. In certain embodiments, the effective amount ranges from about 0.3 mg to about 2 mg. In certain embodiments, the effective amount ranges from about 0.4 mg to about 1.5 mg. In certain embodiments, the effective amount ranges from about 0.5 mg to about 1.25 mg. In certain embodiments, the effective amount ranges from about 0.1 mg to about 1 mg.

In certain embodiments, the effective amount is less than the effective amount delivered by another method, such as, but not limited to, systemic, intracameral, topical, and/or IVT. In certain embodiments, the SCS effective amount is about 90%, or about 75%, or about 50% or less as compared to the effective amount (e.g., about one half or less) delivered by another method, such as, but not limited to, systemic, intracameral, topical, and/or IVT.

The effective amounts per administration described above may be administered in a single administration or in more than 1 administration. Preferably, the effective amounts per administration are in a single administration.

In one embodiment, the drug composition, particularly a fluid drug composition, has a viscosity of less than or equal to 10 Pa*s at a shear rate of 100 $s^{-1}$ when measured under the conditions described herein. In another embodiment, the drug composition, particularly a fluid drug composition, has a viscosity of less than or equal to 1 to 5 Pa*s at a shear rate of 100 $s^{-1}$ when measured under the conditions described herein.

In one embodiment, a suitable drug composition comprises a compound of the disclosure in an amount from about 0.1 to about 5% and about 95% to 99.9% excipients. In another embodiment, a suitable drug composition comprises a compound of the disclosure in an amount from about 0.1 to about 5%, about 90% to 99% water, and about 1% to about 10% additional excipients. In another embodiment, a suitable drug composition comprises a compound of the disclosure in an amount from about 0.1 to about 2.5%, about 90% to 99% water, and about 1% to about 10% additional excipients. In another embodiment, a suitable drug composition comprises a compound of the disclosure in an amount from about 0.1 to about 1%, about 90% to 99% water, and about 1% to about 10% additional excipients. Suitable pharmaceutically acceptable excipients are known in the art. In certain aspects of the above embodiments, the excipient contains at least one polymer. Suitable polymers include, but are not limited to, polyvinylpyrrolidone (for example, PVP K30), tyloxapol, polyethylene glycol (for example, PEG200 to 1000) HA, MC, and CMC.

In certain embodiments, the drug composition is used to localize delivery of a compound of the disclosure to the site of administration (for example, distributed to less than 30% of the SCS) or to provide for a distribution of a compound of the disclosure to 50% or more. To localize delivery at the site of administration, a drug composition may comprise a strongly shear-thinning non-Newtonian drug agent to provide for low viscosity during injection (i.e., high shear) and subsequently provide higher viscosity after injection (i.e., low shear) to prevent further movement. To widely distribute a drug composition throughout the SCS, the drug composition may comprise a moderately shear-thinning non-Newtonian agent to provide low viscosity during injection, but provide only moderate viscosity after injection (for example, such a drug composition may be used for the treatment of macular degeneration, uveitis, diabetic retinopathy, macular edema, and other chorioretinal diseases).

In one aspect of this embodiment, an agent (for example, a polymer or fluid) is considered to be a strongly shear-thinning non-Newtonian fluid if the viscosity (in Pa*s) is equal to or greater than 100 or 200 at a shear rate 0.01 $s^{-1}$ or if the viscosity is equal to or greater 100 Pa*s and less than or equal to 3000 Pa*s at a shear rate of 0.01 $s^{-1}$. In one aspect of this embodiment, a polymer or other fluid is considered to be a strongly shear-thinning non-Newtonian fluid if the viscosity (in Pa*s) is less than 50 at a shear rate 1.0 $s^{-1}$ or if the viscosity is equal to or greater 1 and less than 50 Pa*s at a shear rate of 1.0 $s^{-1}$. When the viscosity of a polymer is determined, the percentage (weight to weight) of the polymer in a solution may be in the range of 1% to 50%, preferably in the range of 1% to 20% or 1% to 10%. Any molecular weight for the polymer may be used.

In one aspect of this embodiment, an agent (for example, a polymer or fluid) is considered to be a moderately shear-thinning non-Newtonian fluid if the viscosity (in Pa*s) is less than 100 at a shear rate 0.01 $s^{-1}$ or if the viscosity is greater than or equal to 1 Pa*s and less than 100 Pa*s at a shear rate of 0.01 $s^{-1}$. In one aspect of this embodiment, a polymer or other fluid is considered to be a moderately shear-thinning non-Newtonian fluid if the viscosity (in Pa*s) is greater than or equal to 50 at a shear rate 1.0 $s^{-1}$ or if the viscosity is greater than or equal to 50 Pa*s and less than 100 Pa*s at a shear rate of 1.0 $s^{-1}$. When the viscosity of a polymer is determined, the percentage (weight to weight) of the polymer in a solution may be in the range of 1% to 50%, preferably in the range of 1% to 20% or 1% to 10%. Any molecular weight for the polymer may be used.

In one embodiment, the moderately and strongly shear thinning agents preferably have a viscosity of less than or equal to 10 Pa*s at a shear rate of 100 $s^{-1}$ when measured under the conditions described herein. In another embodiment, the moderately and strongly shear thinning agents preferably have a viscosity of less than or equal to 1 to 5 Pa*s at a shear rate of 100 $s^{-1}$ when measured under the conditions described herein.

When viscosity measurements are given herein, they are determined using a MCR300 controlled-stress rheometer (Anton Paar, Ashland, VA) equipped with Peltier elements for temperature control and an evaporation blocker that enables measurements of polymer solutions at elevated temperature in a cone-plate geometry. The viscosities of samples are measured at shear rates from 0.01 $s^{-1}$ to 100 $s^{-1}$ at a temperature of 20° C. (samples diluted in deionized water).

An example of a moderately shear thinning polymer is hyaluronic acid (HA), which is extensively used in the eye with an excellent safety record. In one embodiment, HA may be used in a drug composition described herein to provide for distribution of the drug composition to over 50% of the SCS for a period of at least 20 days, at least 40 days, at least 60 days, or at least 90 days or greater after administration. In one aspect of this embodiment, the HA has a molecular weight of between about 300 and about 2000 kDa, between about 500 and about 1500 kDa, or between about 700 and about 1200 kDa. In another aspect of this embodiment, the HA has a molecular weight of about 900 to about 1000 kDa or about 950 kDa. In one aspect of this embodiment, the HA is present in the drug composition at a concentration of about 0.5% to about 10%, about 1% to 7.5%, about 1% to about 5% or about 2.2% (each of the foregoing determined on a weight to volume basis with other components of the drug composition). In another aspect, the HA has a molecular weight in the ranges specified above and is present in the drug composition at the percentage specified above. In another aspect, the HA has a molecular weight of between about 500 and about 1500 kDa and is present at a concentration of about 1% to about 5%. Such a drug composition may further comprise a diluent, such as HBSS, saline, or water.

A non-limiting exemplary drug composition is shown below for a preferred compound of the disclosure, BCX4161.

TABLE 2

| Compound | % w/v | % w/v |
|---|---|---|
| BCX4161 | 0.50% | 0.50% |
| HA (MW 950 kDa) | 2.2% | 2.2% |
| sodium chloride | 0.83% | — |
| disodium phosphate | 0.12% | — |
| WFI | 96.35% | — |
| HBSS | — | 97.3% |

An example of a strongly shear thinning polymer is carboxymethyl cellulose (CMC) or methyl cellulose (MC), which are extensively used in the eye with an excellent safety record. In one embodiment, CMC may be used in a drug composition described herein to provide for distribution of the drug composition to less than 50% of the SCS over a period of 5 to 20 days after administration. In one aspect of this embodiment, the CMC has a molecular weight of between about 25 and about 1500 kDa, between about 100 and about 1200 kDa, or between about 500 and about 1000 kDa. In another aspect of this embodiment, the CMC has a molecular weight of about 600 to about 800 kDa or about 700 kDa. In another aspect of this embodiment, the CMC has a molecular weight of about 50 to about 200 kDa or about 90 kDa. In one aspect of this embodiment, the CMC is present in the drug composition at a concentration of about 0.5% to about 10%, about 1% to 7.5%, about 1% to about 5% or about 1.7% (each of the foregoing determined on a weight to volume basis with other components of the drug composition). In another aspect, the CMC has a molecular weight in the ranges specified above and is present in the drug composition at the percentage specified above. In another aspect, the CMC has a molecular weight of between about 500 and about 1000 kDa and is present at a concentration of about 1% to about 5%. In another aspect, the CMC has a molecular weight of between about 50 and 200 kDa and is present at a concentration of about 1% to about 5%. Such a drug composition may further comprise a diluent, such as MSS, saline, or water.

A non-limiting exemplary drug composition comprising CMC is shown below for a preferred compound of the disclosure, BCX4161.

TABLE 3

| Compound | % w/v | % w/v | % w/v | % w/v |
|---|---|---|---|---|
| BCX4161 | 0.50% | 0.50% | 0.50% | 0.50% |
| CMC (MW 700 kDa) | 1.7% | 1.7% | — | — |
| CMC (MW 90 kDa) | — | — | 1.7% | 1.7% |
| sodium chloride | 0.83% | — | 0.83% | — |
| disodium phosphate | 0.12% | — | 0.12% | — |
| WFI | 96.85% | — | 96.85% | — |
| HBBS | — | 97.8% | — | 97.8% |

In one embodiment, MC may be used in a drug composition described herein to provide for distribution of the drug composition to less than 50% of the SCS over a period of 5 to 20 days after administration. In one aspect of this embodiment, the MC has a molecular weight of between about 25 and about 1500 kDa, between about 100 and about 1200 kDa, or between about 500 and about 1000 kDa. In another aspect of this embodiment, the MC has a molecular weight of about 50 to about 200 kDa or about 90 kDa. In one aspect of this embodiment, the MC is present in the drug composition at a concentration of about 0.5% to about 10%, about 1% to 7.5%, about 1% to about 6% or about 3.0% (each of the foregoing determined on a weight to volume basis with other components of the drug composition). In another aspect, the MC has a molecular weight in the ranges specified above and is present in the drug composition at the percentage specified above. In another aspect, the MC has a molecular weight of between about 50 and about 200 kDa and is present at a concentration of about 1% to about 6%. Such a drug composition may further comprise a diluent, such as MSS, saline, or water.

A non-limiting exemplary drug composition comprising MC is shown below for a preferred compound of the disclosure, BCX4161.

TABLE 4

| Compound | % w/v | % w/v |
|---|---|---|
| BCX4161 | 0.50% | 0.50% |
| MC (MW 90 kDa) | 3.0% | 3.0% |
| sodium chloride | 0.83% | — |
| disodium phosphate | 0.12% | — |
| WFI | 95.55% | — |
| HBSS | — | 96.5% |

In some embodiments, the fluid drug composition includes microparticles or nanoparticles, each of which can include at least one compound of the disclosure and optionally an additional therapeutic agent. When used, the microparticles or nanoparticles may provide for the controlled release of compound of the disclosure and optionally an additional therapeutic agent into the ocular tissue.

The microparticles or nanoparticles may be suspended in an aqueous or non-aqueous liquid excipient. The liquid vehicle may be a pharmaceutically acceptable aqueous solution, and optionally may further include a surfactant. The microparticles or nanoparticles themselves may include an excipient material, such as a polymer, a polysaccharide, a surfactant, etc., which are known in the art to control the kinetics of drug release from such microparticles or nanoparticles.

In certain embodiments, the drug composition further comprises an agent to degrade a component of an ocular tissue. In one embodiment, the agent degrades collagen or glycosaminoglycan fibers in the sclera. Suitable agents for this purpose include, but are not limited to, a hyaluronidase, a collagenase, or a combination thereof. Such degradation may enhance penetration/release of the compound of the disclosure of drug composition into an ocular tissues. Alternatively, the agent that degrades a component of an ocular tissue may be administered to the ocular tissue in a separate step from injection of the compound of the disclosure or drug composition. Such separate step can be preceding and/or following injection of the compound of the disclosure of drug formulation. Preferably, the agent that degrades a component of an ocular tissue and the compound of the disclosure or drug composition are administered at the same site.

In certain embodiments, the drug composition undergoes a phase change or after (preferably with 1 hour or less) injection of the drug composition administration. For instance, a liquid drug composition may be injected through a hollow puncture member into the suprachoroidal space, where it then gels. The compound of the disclosure subsequently diffuses out of or is released from the gelled drug composition to achieve a controlled release of the compound of the disclosure. In certain aspects of this embodiment, the phase change is triggered by a chemical change, such as, but not limited to, a change in pH. In certain aspects of this embodiment, the phase change is triggered by an external stimulus, such as, but not limited to, exposure to light, including specific wavelengths of light, or sound, including specific frequencies.

The volume of the drug composition may also influence how the drug composition diffuses into the suprachoroidal space. Generally, the lower the volume of the drug composition administered, the less the drug composition diffuses away from the site of administration (as compared to a drug composition of the same formulation at a greater volume administered under the same conditions). For example, if a drug formulation comprising 5 μg/μL of a compound of the disclosure in 50 μL HBSS (formulation 1) and a drug formulation comprising 5 μg/μL of a compound of the disclosure in 150 μL HMS (formulation 2) are administered into the suprachoroidal space under the same conditions, then formulation 2 would be expected to be distributed to a greater portion of the suprachoroidal space as compared to formulation 1.

In one embodiment, the volume of drug composition administered into the suprachoroidal space in the methods described herein is from about 10 μL to about 200 μL, such as, but not limited to, from about 50 μL to about 150 μL, 50 μL, 100 μL, or 150 μL. In another embodiment, from about 50 μL to about 500 μL, such as, but not limited to, from about 50 μL to about 300 μL, 200 μL, 250 μL, or 300 μL of the drug composition is administered into the suprachoroidal space. Such volumes may be administered by any of the devices described herein, including, but not limited to, a device incorporating a hollow microneedle.

Methods of Treatment

The present disclosure provides for improved methods of treating ocular diseases or conditions in a subject. In certain embodiments, the drug compositions administered by the methods provided herein achieve delivery of a compound of the disclosure to the suprachoroidal space of the eye, thereby allowing drug access to ocular tissue, particularly, posterior ocular tissues, not obtainable via topical, systemic, intracameral or intravitreal drug delivery. As discussed previously, it is believed that upon entering the SCS the drug formulation flows circumferentially from the insertion site toward the retinochoroidal tissue, macula, and optic nerve in the posterior segment of the eye as well as anteriorly toward the uvea and ciliary body. In addition, a portion of the infused drug formulation may remain in the SCS as a depot, or remain in tissue overlying the SCS, for example the sclera, near the site of administration, serving as additional depot of the compounds of the disclosure that subsequently can diffuse into the SCS and into other adjacent ocular tissues, particularly posterior ocular tissues.

Furthermore, the suprachoroidal drug dose sufficient to achieve a therapeutic response in a human subject treated with the methods provided herein is less than the topical, systemic, intracameral or intravitreal drug dose sufficient to elicit the same or substantially the same therapeutic response.

In certain embodiments, the methods provided herein allow for the delivery of drug formulation over a defined ocular tissue area, particularly a defined posterior ocular tissue area, and to more difficult to target tissue in a single administration as compared to previously known methods.

In a first embodiment, the present disclosure provides a method for treating an ocular disease or condition in a subject, the method comprising non-surgically administering a drug composition comprising an effective amount of a plasma kallikrein inhibitor to the suprachoroidal space (SCS) of the eye of the subject.

In certain aspects of this embodiment, the ocular disease or condition is selected from the group consisting of retinopathy, macular degeneration, uveitis, macular edema, diabetic macular edema, scleritis, retinitis, and choroiditis.

In some embodiments, the macular degeneration is selected from the group consisting of age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, subfoveal wet age-related macular degeneration, and vitreomacular adhesion associated with neovascular age related macular degeneration.

In certain aspects of this embodiment, the retinopathy is selected from the group consisting of diabetic retinopathy, hypersensitive retinopathy, sickle cell retinopathy, retinopathy of prematurity, and central serous retinopathy.

In certain aspects of this embodiment, the neovascular condition is selected from the group consisting of aberrant ocular angiogenesis, ocular neovascularization, choroidal neovascularization, and polypoidal choroidal vasculopathy.

In certain aspects of this embodiment, the ocular disease or condition is a disease or condition of a posterior ocular tissue.

In certain aspects of this embodiment, the ocular disease or condition is a diabetic eye disease or condition.

In a second embodiment, the present disclosure provides a method for treating a neovascular condition in a subject, the method comprising non-surgically administering a drug composition comprising an effective amount of a plasma kallikrein inhibitor to the SCS of an eye of the subject.

In certain aspects of this embodiment, the neovascular condition is selected from the group consisting of aberrant ocular angiogenesis, ocular neovascularization, choroidal neovascularization, and polypoidal choroidal vasculopathy.

In a third embodiment, the present disclosure provides a method for treating a retinopathy in a subject, the method comprising non-surgically administering a drug composition comprising an effective amount of a plasma kallikrein inhibitor to the SCS of an eye of the subject.

In certain aspects of this embodiment, the retinopathy is selected from the group consisting of diabetic retinopathy, hypersensitive retinopathy, sickle cell retinopathy, retinopathy of prematurity, and central serous retinopathy.

In a fourth embodiment, the present disclosure provides a method for treating macular degeneration in a subject, the method comprising non-surgically administering a drug composition comprising an effective amount of a plasma kallikrein inhibitor to the SCS of an eye of the subject.

In a fifth embodiment, the present disclosure provides a method for treating diabetic retinopathy in a subject, the method comprising non-surgically administering a drug composition comprising an effective amount of a plasma kallikrein inhibitor to the SCS of an eye of the subject.

In a sixth embodiment, the present disclosure provides a method for treating diabetic macular edema in a subject, the method comprising non-surgically administering a drug composition comprising an effective amount of a plasma kallikrein inhibitor to the SCS of an eye of the subject.

In a seventh embodiment, the present disclosure provides a method for inhibiting plasma kallikrein activity in a subject, the method comprising non-surgically administering an effective amount of a drug composition comprising a plasma kallikrein inhibitor to the SCS of the eye of the subject. In one aspect of the seventh embodiment, the inhibiting step is used to treat an ocular disease or condition specified in the first embodiment.

In one aspect of any of the foregoing first to seventh embodiments, the subject is determined to be in need of treatment.

In one aspect of any of the foregoing first to seventh embodiments, the drug composition is administered 1 to 12 times per year, preferably 2 to 6 times per year, more preferably 2 or 3 times per year.

In one aspect of any of the foregoing first to seventh embodiments, the drug composition is administered at a dosing interval. Suitable dosing intervals include every month, every 2 months, every 3 months, every 4 months, every 5 months, every 6 months, or up to every 12 months. In one aspect of any of the foregoing first to seventh embodiments, the drug composition is administered at a dosing interval of 3 months, 4 months, 5 months or 6 months (i.e., the drug composition is administered 2 to 4 times per year).

In one aspect of any of the foregoing first to seventh embodiments, administration of the drug composition provides for a concentration of the compound of the disclosure in the SCS or an ocular tissue (such as a posterior ocular tissue) above a minimum therapeutic level over all or substantially all of a dosing interval. Such a dosing interval may be every month, every 2 months, every 3 months, every 4 months, every 5 months, every 6 months, or up to every 12 months. Such minimum therapeutic level may from about 20 ng/ml to about 60 ng/ml, from about 30 to about 55 ng/ml, or from about 40 ng/ml to about 50 ng/ml.

In one aspect of any of the foregoing first to seventh embodiments, administration of the drug composition provides for a concentration of the compound of the disclosure in the SCS or an ocular tissue (such as a posterior ocular tissue) above 20 ng/ml for at least 3 months after administration, at least 4 months after administration, or at least 6 months after administration.

In one aspect of any of the foregoing first to seventh embodiments, administration of the drug composition provides for a concentration of the compound of the disclosure in the SCS or an ocular tissue (such as a posterior ocular tissue) above 30 ng/ml for at least 3 months after administration, at least 4 months after administration, or at least 6 months after administration.

In one aspect of any of the foregoing first to seventh embodiments, administration of the drug composition provides for a concentration of the compound of the disclosure in the SCS or an ocular tissue (such as a posterior ocular tissue) above 40 ng/ml for at least 3 months after administration, at least 4 months after administration, or at least 6 months after administration.

In one aspect of any of the foregoing first to seventh embodiments, administration of the drug composition provides for a concentration of the compound of the disclosure in the SCS or an ocular tissue (such as a posterior ocular tissue) above 50 ng/ml for at least 3 months after administration, at least 4 months after administration, or at least 6 months after administration.

In one aspect of any of the foregoing first to seventh embodiments, administration of the drug composition provides for a concentration of the compound of the disclosure in the SCS or an ocular tissue (such as a posterior ocular tissue) above 100 ng/ml for at least 3 months after administration, at least 4 months after administration, or at least 6 months after administration.

In one aspect of any of the foregoing first to seventh embodiments, administration of the drug composition provides for a concentration of the compound of the disclosure in the SCS or an ocular tissue (such as a posterior ocular tissue) above 250 ng/ml for at least 3 months after administration, at least 4 months after administration, or at least 6 months after administration.

In one aspect of the first to seventh embodiments, the drug composition comprises a moderately shear thinning polymer, such as, but not limited to, HA. In one aspect of the first to seventh embodiments, the drug composition provides for distribution of the drug composition to cover about 50% or more of the SCS, about 70% or more of the SCS, or about 90% or more of the SCS. In another aspect of the first to seventh embodiments, such distribution occurs within 10 days of administration and is maintained for a period of at least 20 days, at least 40 days, at least 60 days, or at least 90 days or greater after administration. In one aspect of the first to seventh embodiments, the drug composition is as described in Table 2.

In one aspect of the first to seventh embodiments, the drug composition comprises a strongly shear thinning polymer, such as, but not limited to, CMC or MC. In one aspect of the first to seventh embodiments, the drug composition provides for distribution of the drug composition to cover less than 50% of the SCS, less than about 35% of the SCS, or less than about 25% of the SCS. In another aspect of the first to seventh embodiments, such distribution is limited to a period of from administration to 20 days after administration. In one aspect of the first to seventh embodiments, the drug composition is as described in Table 3 or Table 4.

In one aspect of the first to seventh embodiments, administration of the drug composition provides a therapeutic benefit in the treatment of the ocular disease or condition in the absence of a local and/or a systemic side effect.

In one aspect of the first to seventh embodiments, the compound of the disclosure is targeted to the posterior segment of the eye. In one aspect of the first to seventh embodiments, the compound of the disclosure is present in at least a 10-fold to 100-fold higher in a posterior tissue of the eye as compared to the aqueous humor 14 days, 28, days, 56 days or 84 days after administration.

In any of the foregoing aspects of embodiments, the ocular tissue is the sclera, the choroid, the Bruch's membrane, the RPE, the subretinal space, the retina, the macula, the optic disk, the optic nerve, the ciliary body, and/or the trabecular meshwork. More preferably, in any of the foregoing embodiments or aspects of embodiments, the ocular tissue is the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina.

In one aspect of any of the foregoing first to seventh embodiments, administration of the drug composition provides for a concentration of the compound of the disclosure in the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina above 20 ng/ml for at least 3 months after administration, at least 4 months after administration, or at least 6 months after administration.

In one aspect of any of the foregoing first to seventh embodiments, administration of the drug composition provides for a concentration of the compound of the disclosure in the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina above 30 ng/ml for at least 3 months after administration, at least 4 months after administration, or at least 6 months after administration.

In one aspect of any of the foregoing first to seventh embodiments, administration of the drug composition provides for a concentration of the compound of the disclosure in the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina above 40 ng/ml for at least 3 months after administration, at least 4 months after administration, or at least 6 months after administration.

In one aspect of any of the foregoing first to seventh embodiments, administration of the drug composition provides for a concentration of the compound of the disclosure in the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina above 50 ng/ml for at least 3 months after administration, at least 4 months after administration, or at least 6 months after administration.

In one aspect of any of the foregoing first to seventh embodiments, administration of the drug composition provides for a concentration of the compound of the disclosure in the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina above 100 ng/ml for at least 3 months after administration, at least 4 months after administration, or at least 6 months after administration.

In one aspect of any of the foregoing first to seventh embodiments, administration of the drug composition provides for a concentration of the compound of the disclosure in the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina above 250 ng/ml for at least 3 months after administration, at least 4 months after administration, or at least 6 months after administration.

In one aspect of the first to seventh embodiments, the compound of the disclosure is retained in an ocular tissue, such as, but not limited to, the sclera, the choroid, the Bruch's membrane, the RPE, the retina, the macula, the peripheral RPE, the peripheral choroid, the peripheral sclera, the peripheral retina, the central RPE, the central choroid, the central sclera, and/or the central retina, for an extended length of time. For example, in some aspects, the compound of the disclosure is retained in the ocular tissue for at least about 7, 14, 21, 28, 35, 42, 49, 56, 63, 70, 90, or more days after administration.

In one aspect of the first to seventh embodiments, the plasma kallikrein inhibitor is a small molecule plasma kallikrein inhibitor, an inhibitory peptide, or an anti-plasma kallikrein antibody, or fragment thereof. In one aspect of the first to seventh embodiments, the plasma kallikrein inhibitor is a compound of the formula I or a compound of the formula IB. In one aspect of the first to seventh embodiments, the plasma kallikrein inhibitor is BCX4161.

The plasma kallikrein inhibitor delivered to the SCS via the methods described herein, particularly the methods of the first to seventh embodiment, for the treatment of one or more ocular diseases and conditions, can be administered with one or more additional therapeutic agents. The one or more additional therapeutic agents may be present in the same drug composition as the plasma kallikrein inhibitor or may be delivered in a separate formulation. The one or more additional therapeutic agents may be delivered to the SCS or may be delivered intravitreally, intracamerally, topically or systemically to the subject. In one embodiment, an angiogenesis inhibitor, such as, but not limited to, a VEGF antagonist, is administered to the SCS of the eye of a subject in conjunction with a compound of the disclosure.

Determining Therapeutic Efficacy

The therapeutic efficacy of the drug compositions delivered by the methods described herein and therapeutic response of the subject can be assayed by standard means in the art, as known to those of skill in the art. In general, the therapeutic efficacy of a drug composition and/or a compound of the disclosure can be assessed by measuring the response of the subject after administration of the drug composition and/or the compound of the disclosure. A drug composition and/or a compound of the disclosure with a high therapeutic efficacy will show a greater amelioration and/or discontinuation of symptoms than a drug composition and/or a compound of the disclosure with a lower therapeutic efficacy. The therapeutic efficacy is dependent on not only the drug formulation and the compound of the disclosure, but also on the condition being treated and the severity of the condition being treated. In non-limiting examples, the efficacy of the drug compositions provided herein can be measured, for example, by observing changes in pain intensity, ocular lesions (size or number), cell death, intraocular pressure, inflammation (for example, by measuring changes in the Hackett/McDonald ocular score), ocular hypertension, edema, changes in retinal thickness (for example, changes in optical coherence tomography (OCT) measurements of retinal thickness and volume), photophobia, time between flares, corneal ulceration, and/or visual acuity.

EXAMPLES

Example 1: Evaluation of PK and Ocular Tolerability of a BCX4161 Suspension Following Suprachoroidal Administration Dutch belted rabbits were used in the study. A 0.5% w/v suspension of BCX4161 was prepared as shown in Table 5 below.

TABLE 5

| Compound | % w/v |
|---|---|
| BCX4161 | 0.50% |
| sodium chloride | 0.83% |
| povidone (K30) | 2.07% |
| tyloxapol | 0.31% |
| disodium phosphate | 0.12% |
| hydrochloric acid | 0.00% |
| sodium hydroxide | 0.00% |
| WFI | 96.17% |

100 μL of the suspension was administered bilaterally to the suprachoroidal space of the eye, at a dose of 0.5 mg/eye. Two rabbits (4 eyes) were treated per time point, except at day 28, when 3 rabbits were treated. Plasma was collected at 3 hours, 1 day, 3 days, 7 days, 10 days, 14 days, 21 days, 28 days, 56 days, and 84 days post-dose. Aqueous humor, vitreous humor, peripheral retina, peripheral sclera/choroid/RPE, central retina, and central sclera/choroid/RPE punch punch tissues were collected at 1 day, 7 days, 14 days, 28 days, 56 days and 84 days post-dose. Ocular examinations and intraocular pressure (IOP) were also assessed, anterior and posterior segments, at 1 day, 7 days, 14 days, 28 days, 56 days, and 84 days post-dose. Redness, chemosis, discharge, opacity, aqueous flare, cellular flare, vitreous flare, retinal vasculature, retinal and choroidal pathology were assessed at those time points.

The results of the study showed that a 0.5% suspension of BCX4161 was well tolerated and had a highly favorable PK profile after a single SCS injection for at least 3 months, making SCS administration of plasma kallikrein inhibitors a safe and durable treatment for a variety of ocular diseases and conditions.

Mild conjunctival redness and chemosis was observed on day 1 post-dose. No adverse events were observed on days 7, 14, 28, 56, or 84 post-dose. The ocular exam score was 0 for all observations.

BCX4161 administered via SCS injection showed a favorable ocular PK profile, as shown in FIGS. 1-5. High drug levels were achieved in both the central and peripheral RPE/choroid/sclera (FIG. 1). BCX4161 reached the optic nerve region, closer to the macula (central RPE/choroid/sclera) and was present at high drug levels in both the central and peripheral RPE/choroid/sclera for at least up to 84 days after SCS injection.

Figure 2:
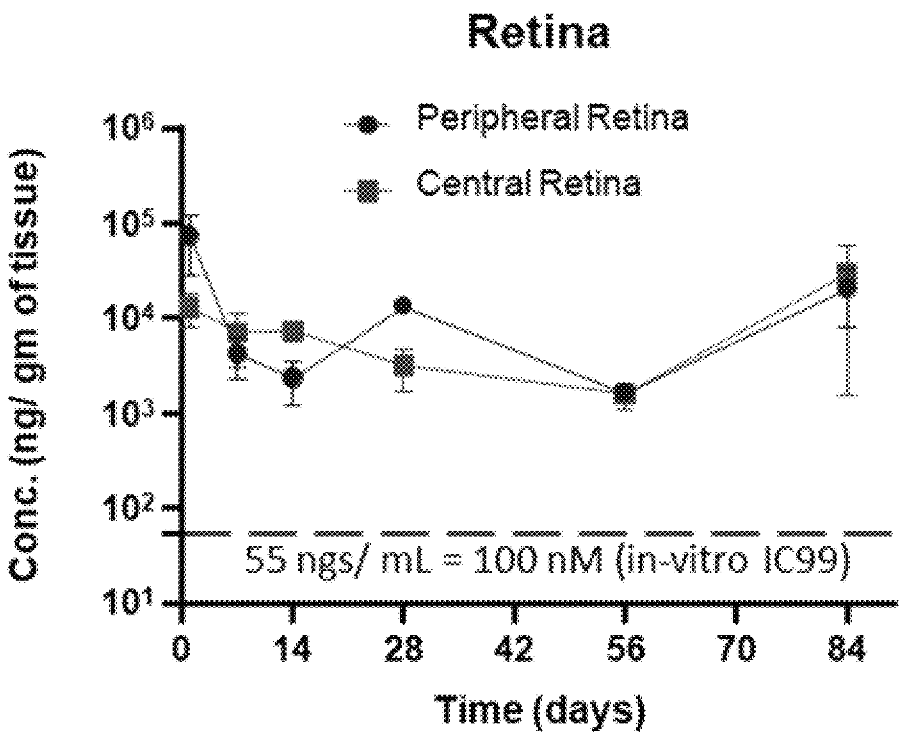
FIG. 2 shows drug concentration (ng/gram of tissue) in the peripheral retina (circles) and central retina (squares) following SCS injection of BCX4161 (0.5 mg/eye). Results are shown as the mean±the SEM; n=4 at each time point unless otherwise noted.

High levels of BCX4161 were also achieved in the both the central and peripheral retina (FIG. 2). BCX4161 was present at high drug levels in both the central and peripheral retina for at least up to 84 days after SCS injection. The dotted line in FIG. 2 represents the $IC_{99}$ value for BCX4161 inhibition of plasma kallikrein in vitro, illustrating that the concentrations obtained are well above the levels required for effective inhibition of plasma kallikrein. Concentrations of plasma kallikrein inhibitors above the $IC_{99}$ value have previously shown to correlate with effective therapy in vivo.

Figure 3A:
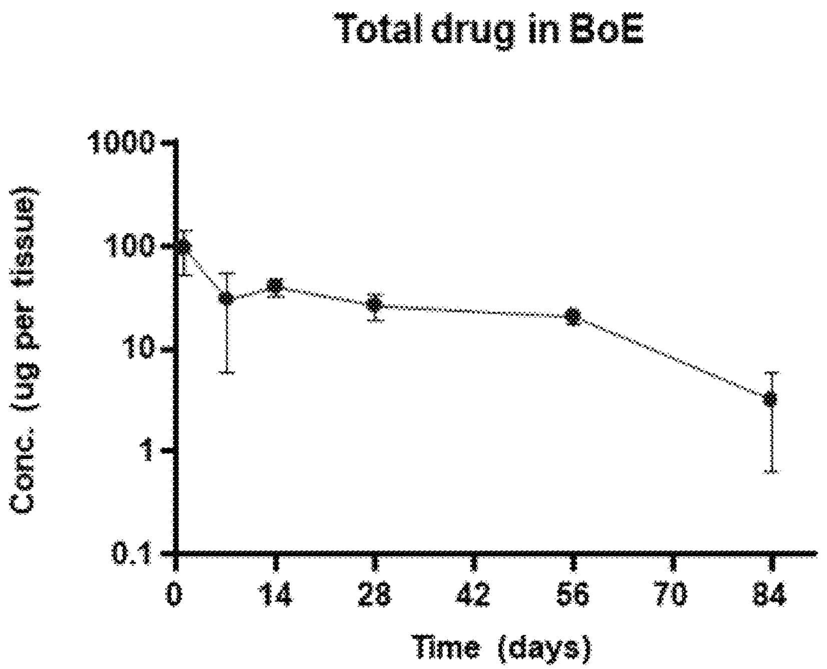
FIG. 3A shows drug concentration (μg/tissue) in the back of the eye (BoE) tissue over time following SCS injection of BCX4161 (0.5 mg/eye). Results are shown as the mean±the SEM; n=4 at each time point unless otherwise noted.
Figure 3B:
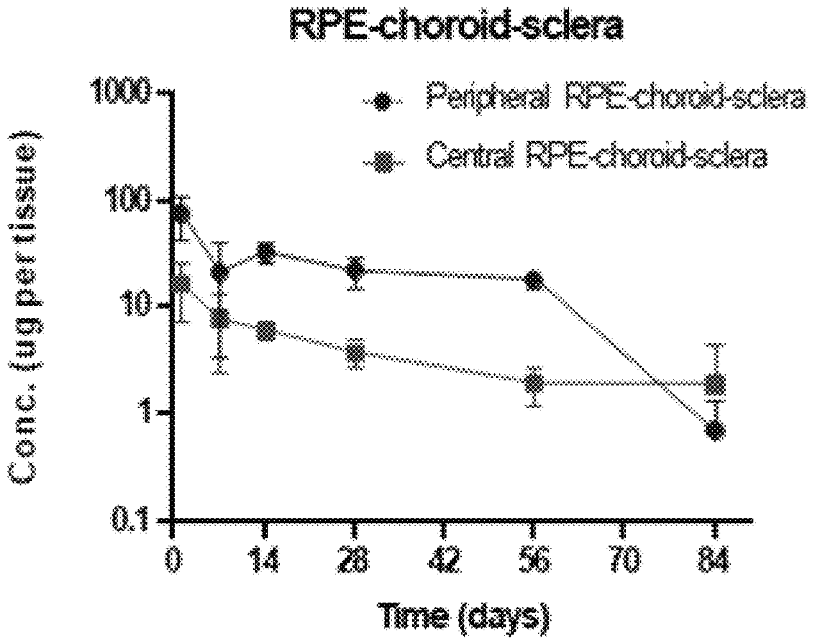
FIG. 3B shows drug concentration (μg/tissue) in the peripheral RPE/choroid/sclera (circles) and central RPE/choroid/sclera (squares) over time following SCS injection of BCX4161 (0.5 mg/eye). Results are shown as the mean±the SEM; n=4 at each time point unless otherwise noted.
Figure 3C:
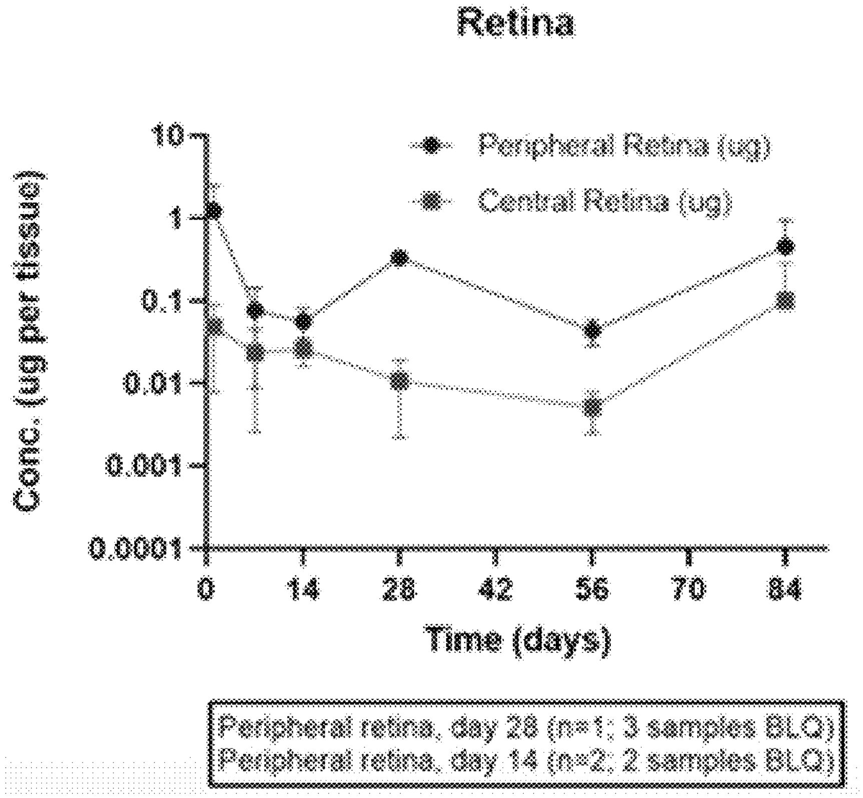
FIG. 3C shows drug concentration (μg/tissue) in the peripheral retina (circles) and central retina (squares) over time following SCS injection of BCX4161 (0.5 mg/eye). Results are shown as the mean±the SEM; n=4 at each time point unless otherwise noted.

FIGS. 3A-C show the drug concentration of BCX4161 in total and selected back of the eye tissues. FIG. 3A shows the concentration of BCX4161 in the back of the eye tissues, with FIG. 3B showing the concentration of BCX4161 in the peripheral and central RPE/choroid/sclera and FIG. 3C showing the concentration of BCX4161 in the peripheral and central retina.

Figure 4A:
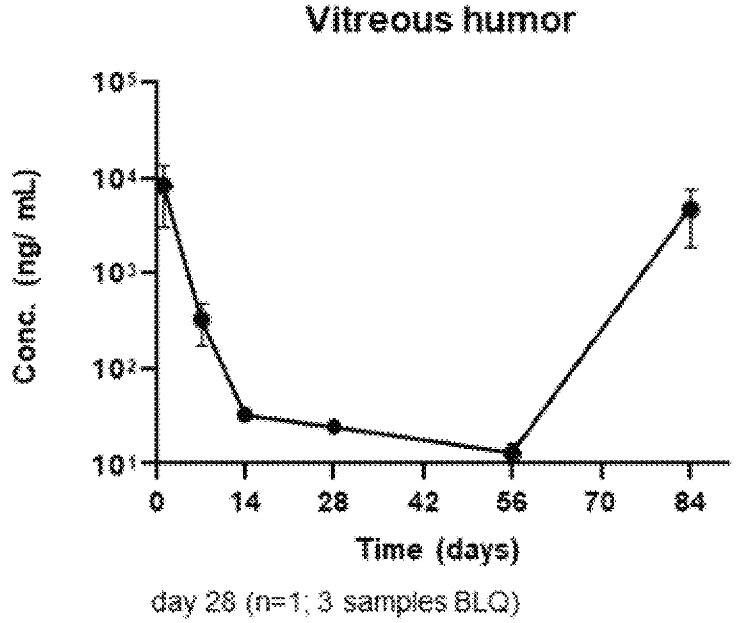
FIG. 4A shows drug concentration (ng/ml) in the vitreous humor over time following SCS injection of BCX4161 (0.5 mg/eye). Results are shown as the mean±the SEM; n=4 at each time point unless otherwise noted.
Figure 4B:
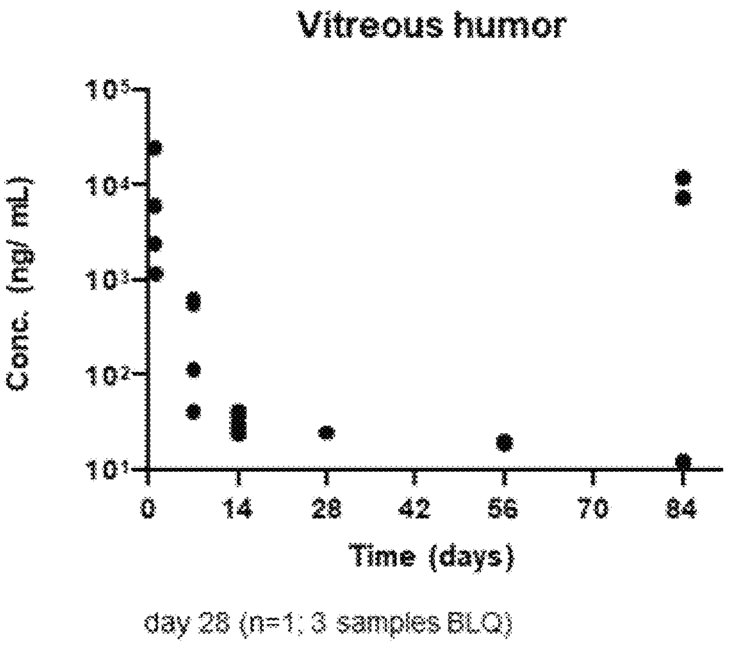
FIG. 4B shows drug concentration (ng/ml) in the vitreous humor over time following SCS injection of BCX4161 (0.5 mg/eye). Results are shown for each time point individually with n=4 at each time point unless otherwise noted.
Figure 4C:
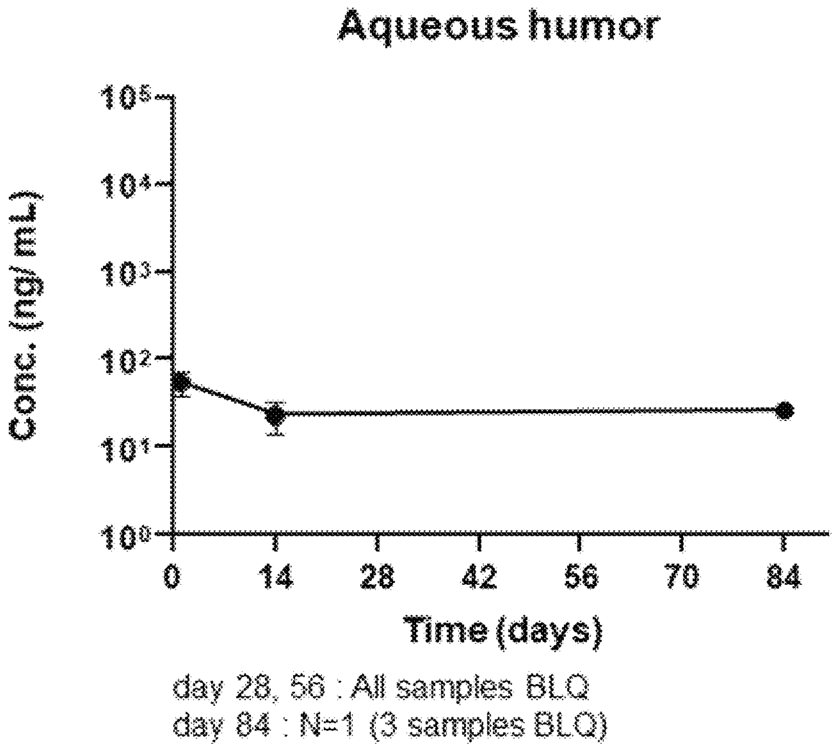
FIG. 4C shows drug concentration (ng/ml) in the aqueous humor over time following SCS injection of BCX4161 (0.5 mg/eye). Results are shown as the mean±the SEM; n=4 at each time point unless otherwise noted.
Figure 5:
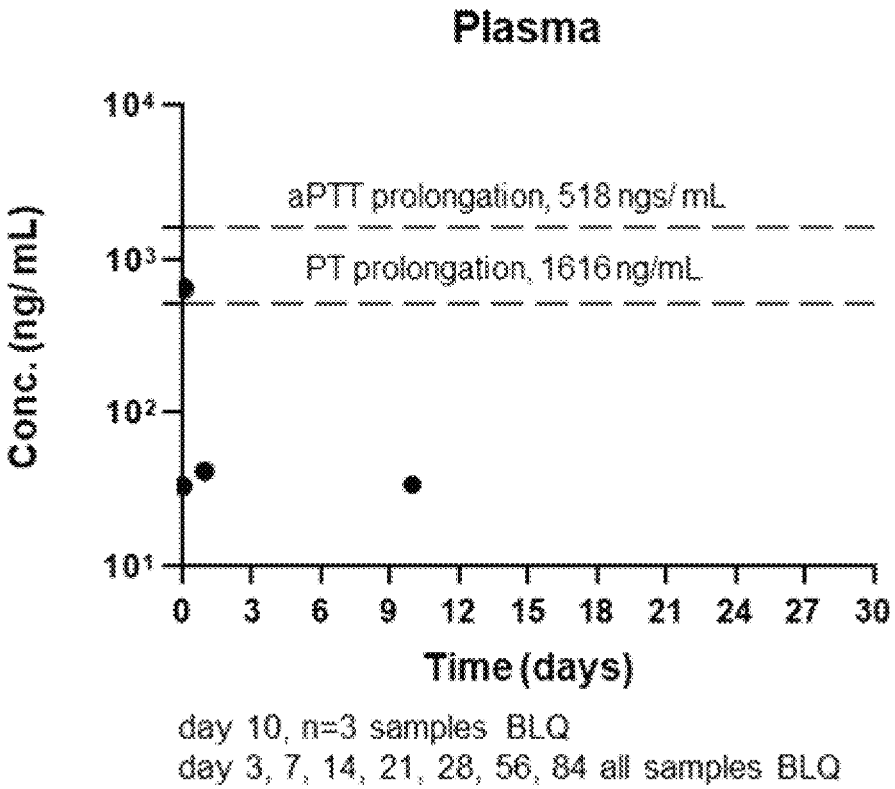
FIG. 5 shows the systemic drug concentration (ng/ml) over time following SCS injection of BCX4161 (0.5 mg/eye). Results are shown as the mean±the SEM; n=4 at each time point unless otherwise noted.

There were moderate to low levels of BCX4161 in the vitreous humor (FIGS. 4A and 4B). In addition, there were low levels of BCX4161 in the aqueous humor (FIG. 4C), showing there was limited drug exposure to the anterior segment (front) of the eye. FIG. 4B shows the individual data points used to generate the graph of FIG. 4A, illustrating two outlier value at day 84. BCX4161 also showed a favorable systemic PK profile (FIG. 5). There was minimal to no systemic exposure, and thus the risk of systemic effects is reduced or eliminated (noting that in humans, the dilution factor is significantly greater than in rabbits).

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls. While the described invention has been described with reference to the specific embodiments thereof it should be understood by those skilled in the art that various changes may be made and equivalents may be substituted without departing from the true spirit and scope of the disclosure. In addition, many modifications may be made to adopt a particular situation, material, composition of matter, process, process step or steps, to the objective spirit and scope of the described disclosure. All such modifications are intended to be within the scope of the claims appended hereto.

What is claimed:

1. A method for treating an ocular disease or condition in a subject, the method comprising non-surgically administering an effective amount of a drug composition comprising an effective amount of a plasma kallikrein inhibitor to a suprachoroidal space (SCS) of an eye of the subject thereby allowing the plasma kallikrein inhibitor access to an ocular tissue, wherein the plasma kallikrein inhibitor is the sole therapeutic agent present in the drug composition, and wherein the ocular disease or condition is diabetic retinopathy or diabetic macular edema, and wherein the plasma kallikrein inhibitor is a compound of formula IB

IB

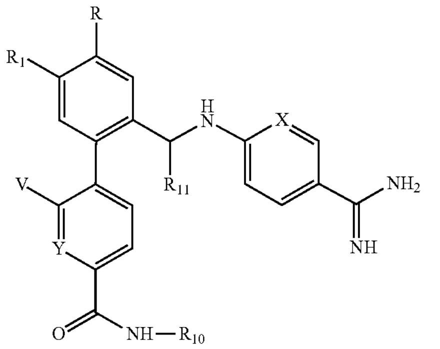

wherein:

X is CH;

Y is N;

R is $—CH_2═CH_2$;

$R_1$ is $—OCH_3$;

V is C(O)OH;

$R_{10}$ is $—(CH_2)$-cyclopropyl; and $R_{11}$ is ═O.

2. The method of claim 1, wherein the drug composition is administered 2 to 6 times per year or 2 or 3 times per year.

3. The method of claim 1, wherein administration of the drug composition provides for a concentration of the plasma kallikrein inhibitor in the SCS or an ocular tissue above a minimum therapeutic level over all or substantially all of a dosing interval.

4. The method of claim 3, wherein the dosing interval is selected from the group consisting of: every month, every 2 months, every 3 months, every 4 months, every 5 months, every 6 months, and every 12 months.

5. The method of claim 3, wherein the ocular tissue is a posterior ocular tissue.

6. The method of claim 5, wherein the posterior ocular tissue is the sclera, the choroid, the Bruch's membrane, the retinal pigment epithelium (RPE), the retina, the macula, the peripheral RPE, the peripheral choroid, the peripheral sclera, the peripheral retina, the central RPE, the central choroid, the central sclera, the central retina, or a combination of the foregoing.

7. The method of claim 3, wherein the dosing interval is every 2 months.

8. The method of claim 3, wherein the dosing interval is every 3 months.

9. The method of claim 1, wherein a volume of the drug composition administered is from about 10 μL to about 200 μL.

10. The method of claim 1, wherein administration of the drug composition provides a therapeutic benefit in the treatment of the ocular disease or condition in the absence of a local or a systemic side effect.

11. The method of claim 1, wherein the effective amount of the plasma kallikrein inhibitor in the drug composition ranges from about 0.01 mg to about 20 mg.

12. The method of claim 1, wherein the effective amount of the plasma kallikrein inhibitor in the drug composition ranges from about 0.1 mg to about 10 mg.

13. The method of claim 1, wherein the effective amount of the plasma kallikrein inhibitor in the drug composition ranges from about 0.1 mg to about 1 mg.

14. The method of claim 1, wherein the ocular disease or condition affects a posterior segment of the eye.

15. The method of claim 1, wherein the drug composition is administered to the SCS of the eye via a hollow microneedle.

16. The method of claim 1, further comprising administering an additional therapeutic agent.

* * * * *